United States Patent
Plumptre et al.

(10) Patent No.: US 10,293,113 B2
(45) Date of Patent: May 21, 2019

(54) DRIVE MECHANISM FOR AN INJECTION DEVICE

(71) Applicant: SANOFI-AVENTIS DEUTSCHLAND GMBH, Frankfurt am Main (DE)

(72) Inventors: David Aubrey Plumptre, Worcestershire (GB); Robert Veasey, Warwickshire (GB); John David Cross, Northhamptonshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 78 days.

(21) Appl. No.: 15/548,503

(22) PCT Filed: Feb. 10, 2016

(86) PCT No.: PCT/EP2016/052764
§ 371 (c)(1),
(2) Date: Aug. 3, 2017

(87) PCT Pub. No.: WO2016/128424
PCT Pub. Date: Aug. 18, 2016

(65) Prior Publication Data
US 2018/0236176 A1   Aug. 23, 2018

(30) Foreign Application Priority Data

Feb. 10, 2015 (EP) ..................... 15154487

(51) Int. Cl.
*A61M 5/00* (2006.01)
*A61M 5/315* (2006.01)

(52) U.S. Cl.
CPC .... *A61M 5/31541* (2013.01); *A61M 5/31535* (2013.01); *A61M 5/31543* (2013.01);
(Continued)

(58) Field of Classification Search
CPC .......... A61M 5/31541; A61M 5/31543; A61M 5/31551; A61M 2205/581;
(Continued)

(56) References Cited

U.S. PATENT DOCUMENTS

2013/0289518 A1* 10/2013 Butler ............... A61M 5/31535
604/500

FOREIGN PATENT DOCUMENTS

WO   WO 2012/049138   4/2012
WO   WO 2012/049139   4/2012
(Continued)

OTHER PUBLICATIONS

International Search Report and Written Opinion in International Application No. PCT/EP2016/052764, dated Jun. 3, 2016, 13 pages.
(Continued)

*Primary Examiner* — Jason E Flick
(74) *Attorney, Agent, or Firm* — Fish & Richardson P.C.

(57) ABSTRACT

The present disclosure relates to a drive mechanism for an injection device for setting and dispensing of a dose of a medicament, the drive mechanism comprising:
- an inner body fixable inside a housing of the injection device, the inner body comprising an elongated shaft extending in an axial direction (z) and having an outer thread,
- a tubular-shaped display member having an inner thread engaged with the outer thread of the inner body, and
- a dose member axially displaceable between a dose setting position (S) and a dose dispensing position (D) relative to the display member,
wherein the display member comprises at least one blocking member movable in axial direction (z) between a blocking position (B) and a release position (R) and engageable with a blocking structure on the outer circumference of the inner body, (Continued)

wherein when in blocking position (B) the blocking member axially engages with the dose member and with the blocking structure to block an axial displacement of the dose member from the dose setting position (S) towards the dose dispensing position (D).

17 Claims, 13 Drawing Sheets

(52) U.S. Cl.
CPC .... *A61M 5/31551* (2013.01); *A61M 5/31585* (2013.01); *A61M 5/31575* (2013.01); *A61M 2205/581* (2013.01); *A61M 2205/582* (2013.01)

(58) Field of Classification Search
CPC ........ A61M 2205/582; A61M 5/31535; A61M 5/31575; A61M 5/31585

USPC .......................................................... 604/207
See application file for complete search history.

(56) References Cited

FOREIGN PATENT DOCUMENTS

| WO | WO 2012/049140 | 4/2012 |
| WO | WO 2014/033195 | 3/2014 |
| WO | WO 2014/033197 | 3/2014 |

OTHER PUBLICATIONS

International Preliminary Report on Patentability in International Application No. PCT/EP2016/052764, dated Aug. 15, 2017, 9 pages.

* cited by examiner

DRIVE MECHANISM FOR AN INJECTION DEVICE

CROSS-REFERENCE TO RELATED APPLICATIONS

This application is a U.S. national stage application under 35 USC § 371 of International Application No. PCT/EP2016/052764, filed on Feb. 10, 2016, which claims priority to European Patent Application No. 15154487.1, filed on Feb. 10, 2015, the entire contents of which are incorporated herein by reference.

TECHNICAL FIELD

The present disclosure relates in one aspect to a drive mechanism for an injection device, such like a pen-type injector for setting and dispensing of a dose of a medicament. In particular, the disclosure relates to an injection device providing a minimum dose mechanism, i.e. a dose setting and dispensing mechanism that is only operable to dispense a dose if the dose exceeds a predefined minimum threshold.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easily understandable. Moreover, the dose setting as well as the dose dispensing procedure must be easy to operate and has to be unambiguous.

Typically, such devices comprise a housing including a cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast, injection devices of disposable type are to be discarded when the medicament in the cartridge has been dispensed or used-up.

Documents WO 2014/033197 A1 and WO 2014/033195 A1 disclose disposable and reusable drug delivery devices for selecting and dispensing a number of user variable doses of a medicament. These devices comprise a housing, a cartridge holder for retaining a cartridge containing the medicament, a piston rod displaceable relative to the cartridge holder, a driver coupled to the piston rod, a display member indicating a set dose and being coupled to a housing and to the driver, and a button coupled to the display member and to the driver.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential pre-fixed doses of a medication may be required. For example the range of doses may be needed to satisfy the therapeutic needs of different user groups, or to allow individual users to deliver a different dose at different times of the day e.g. in the morning or in the evening.

Certain aspects of the present disclosure can be implemented to provide a drive mechanism for an injection device that provides a minimum dose function. Certain aspects of the drive mechanism can also provide a maximum dose function. It is a further aim to provide a drive mechanism that allows for priming of the device, so that a user is able to dial and to deliver a rather small volume of medication, typically 2 international units (IU), to check whether flow occurs correctly through a needle assembly, that is releasably attachable to a distal dispensing end of the device.

Implementation of the desired minimum and/or maximum dose function should be achievable by modifying only a limited number of existing device components. It is a further aim to individually modify minimum and maximum dose values or dose sizes by changing only a single or only a few components of the device. Hence, the minimum and/or maximum dose function of the device or its drive mechanism should be configurable by interchanging only one or a few components of the device or its drive mechanism. It is a further aim, that the improved drive mechanism is universally applicable to a large variety of drive mechanisms and injection devices. In particular, the improved drive mechanism should be equally applicable to disposable injection devices as well as to reusable injection devices. Furthermore, and in one embodiment, the drive mechanism should be operable as a so-called fixed dose mechanism exclusively operable to set and to dispense a single or multiple doses of a pre-defined, hence 'fixed' size.

SUMMARY

In a first aspect the disclosure relates to a drive mechanism for an injection device. The injection device is operable to set and to dispense multiple doses of variable size of a medicament, typically by way of injection. The drive mechanism of the injection device comprises the mechanically inter engaging components that are required to exert distally directed thrust to a piston of a cartridge filled with the liquid medicament. The drive mechanism comprises an inner body that is fixable inside a housing of the injection device. The inner body at least comprises an elongated shaft that extends in an axial direction (z) and having an outer thread. The outer thread is a helical thread and has a constant or varying pitch in the axial direction. The inner body is fixable inside the housing in a non-movable way. Hence, the inner body is axially as well as rotationally fixable inside a tubular or cylindrically-shaped housing of the injection device. The inner body and the housing may also be integrally formed. Hence, the inner body may be a portion of the housing.

The drive mechanism further comprises a tubular-shaped display member having an inner thread engaged or mating with the outer thread of the inner body. The tubular-shaped display member is axially displaceable relative to the inner body, in particular relative to its elongated shaft when rotating in a helical way. Typically, the pitch and friction of the threaded engagement of the display member and the inner body is such that the display member starts to rotate when it is subject to an axial force effect relative to the inner body.

In addition, the drive mechanism comprises a dose member that is axially displaceable between a dose setting position (S) and a dose dispensing position (D) relative to the display member. The dose member may be rotatable relative to the inner body. It may be also axially displaceable relative to the inner body. Typically, the dose member is rotatable along a helical path relative to the inner body for setting of a dose. Moreover, the dose member may be axially displaceable in a non-rotative manner relative to the inner body for dispensing of a dose. The dose member and the display member may be selectively rotationally engaged, typically by means of a clutch by way of which the rotational engagement between dose member and display member is either locked or released.

In a dose setting mode the clutch is typically closed, so that a torque applied to the dose member is transferred to the display member, which upon its threaded engagement with the inner body is then displaced axially relative to the inner body in unison with the dose member. For dose dispensing the clutch between display member and dose member may be released so that the display member may rotate when returning into its initial position while the dose member is subject to a purely translational displacement. Hence, during dose dispensing the dose member may be rotationally locked to the inner body while the display member is free to rotate relative to the display body and hence relative to the dose member.

Depending on the specific embodiment of the drive mechanism either the rotating display member or the translationally displacing dose member is operably engaged with the piston rod for driving the piston rod in a distal dose dispensing direction during dose dispensing for displacing the piston of the cartridge in the distal direction.

The display member further comprises at least one blocking member that is movable and/or flexible in the axial direction between a blocking position (B) and a release position (R). The blocking member is engageable with a blocking structure that is located on the outer circumference of the inner body. Typically, the blocking structure is located on the outer circumference of the elongated shaft of the inner body. The radial extension of the blocking structure typically coincides or is substantially equal to the radial extension of the elongated shaft's outer thread. In other embodiments the radial extension of the blocking structure may exceed the radial extension of the outer thread.

When in a blocking position (B) the blocking member axially engages with the dose member and with the blocking structure. In this blocking position the dose member is effectively blocked and is therefore unable to be axially displaced relative to the inner body or relative to the dose member from the dose setting position towards the dose dispensing position. Hence, when the blocking member of the display member engages the blocking structure of the inner body, which may typically occur during a dialing or helical rotative motion during dose setting, the blocking member serves to block a respective axial displacement of the dose member by effectively impeding an axial displacement of the dose member relative to the display member and/or relative to the body or housing. In this blocked condition the clutch between dose member and display member is effectively locked in the closed configuration so that the drive mechanism remains in the dose setting mode, characterized by the dose member being located in the dose setting position (S) relative to the display member.

Depending on the mutual engagement of blocking member and blocking structure and specifically the geometry and extension of the blocking structure, dose dispensing can be effectively blocked for a predefined range of dose sizes. In this way, minimum and maximum thresholds can be defined between which dose dispensing is effectively blocked and impeded. A minimum threshold may define a maximum dose value for a priming procedure, e.g. 2 or 3 IU. A maximum threshold could define a minimum dose size, hence a dose size that has at least to be dispensed by the drive mechanism in order to ensure sufficient delivery of e.g. one element of a combined drug to obtain a desired therapeutic effect.

The blocking member may flex in the axial direction in response to an engagement with the blocking structure. Moreover, the blocking member flexed in an axial direction may be supported and mechanically strengthened by the blocking structure so as to provide a rather strong and robust axial abutment for the dose member. Alternatively, the blocking member may also axially engage with the blocking structure without flexing axially. In such a non-flexed condition it is simply prevented from moving axially relative to the blocking structure. So even in such a non-flexed but engaged configuration, the blocking member engaged with the blocking structure is axially constrained or axially fixed in at least one axial direction relative to the housing, typically in a distal direction. When engaged with the blocking structure the blocking member may also be axially engaged with the dose member, which is then also axially constrained or axially fixed with respect to the housing.

Generally, the blocking member engages on the proximal side of the blocking structure so that it cannot be flexed distally by the dose member whilst engaged with the blocking structure, if the user attempts to dispense a dose.

According to another embodiment the blocking structure comprises a blocking thread on the elongated shaft of the inner body. The blocking thread may extending between convolutions of the outer thread of the inner body but may be also axially separated from the outer thread on the shaft. The blocking thread and the outer thread have the same pitch. Typically, the blocking thread, hence the convolutions of the blocking thread may be located axially midway between neighboring convolutions of the outer thread of the inner body, in particular of its elongated shaft. Since blocking thread and outer thread have the same pitch and since blocking thread and outer thread are axially offset the blocking member remains in its blocking position during engagement with the blocking thread when the display member is subject to a helical rotation relative to the inner body during a dose dialing operation.

Typically, the axial extension of the blocking thread is shorter than the overall axial extension of the outer thread. As seen in an axial direction the blocking thread may be located inside the outer thread, so that proximal and distal ends of the blocking thread are both located in an axial region confined by proximal and distal ends of the outer thread. In alternative embodiments and depending on the axial position of the inner thread of the display member relative to the axial position of the blocking member it is also conceivable that a proximal and/or a distal end of the blocking thread is located beyond a proximal or distal end of the outer thread.

As the display member rotates relative to the inner body the blocking member may flex in an axial direction as it engages with one end of the blocking thread. It may then remain flexed as it slides along the blocking thread and it returns into its release position as it passes the opposite axial end of the blocking thread. When the blocking member has passed the proximal end of the blocking thread during a dose incrementing rotation of the display member relative to the inner body the blocking member may be axially flexed by the dose member under the effect of the dose member advancing distally in the axial direction to dispense a dose. In this condition, the dose member is free to be displaced a distance in the axial direction relative to the display member sufficient to release the clutch between display member and dose member. When the clutch is released, the device is switched into a dose dispensing mode and a dose dispensing procedure may start.

According to a further embodiment the blocking member comprises a flexible arm extending in a tangential direction around the circumference of the display member. The flexible arm of the blocking member may be arc-shaped and may follow the contour of the sidewall of the display member. In order to provide an axial flexing or axial deformation of the blocking member relative to the display member the blocking member is either arranged at an axial end of the display member or it is located in a recess of the sidewall, in which recess it is free to resiliently bend or to pivot in axial direction. The flexible arm does not necessarily have to extend exactly tangentially and perpendicularly to the axial direction of the tubular-shaped display member. It is generally conceivable, that the flexible arm extends at a certain angle with respect to the tangential or circumferential direction and the axial direction of the display member.

Typically, the flexible arm is integrally formed with the display member. The flexible arm may comprise a base portion integrally formed with the blocking member, from which base portion the flexible arm extends towards a free end. Due to the flexibility of the material and the geometry of the flexible arm, it is particularly its free end that is flexible, pivotable or displaceable in an axial direction in order to switch between its blocking position and its release position. Implementation of the blocking member as a flexible arm that substantially coincides with the outer circumference of the display member is a rather space saving and cost efficient solution. Moreover, the integral implementation of the blocking member into the display member only requires modification of one component of the drive mechanism and does not require assembly of additional components.

The same is also valid in regard to the blocking structure. The blocking structure can be implemented into the inner body without the necessity to provide a separate component. The general functionality and behavior of the minimum dose function can be modified by making use of an appropriately configured blocking structure. Modification of the minimum dose function only requires exchange an inner body component with a first blocking structure for a different inner body with an alternative blocking structure.

In another embodiment the blocking member comprises a radially inwardly extending protrusion at a free end section of the flexible arm to engage with the blocking structure. In this way modifying the display member to implement the blocking member has no effect on components of the injection device or the drive mechanism that are arranged at or along the outer circumference of the display member. Moreover, by means of the radially inwardly extending protrusion the free end of the blocking member's flexible arm is axially displaceable as it engages with the blocking thread of the blocking structure. Further, by means of the inwardly extending protrusion the blocking member's free end may be axially supported and axially constrained when in axial abutment or axial engagement with the blocking structure. Any distally directed forces transferred from the dose member to the display member are then counter-acted by the axial abutment of the blocking member's inwardly extending protrusion when in axial abutment or axial engagement with the blocking structure. Depending on the geometry or slope of the blocking structure in comparison to the slope and geometry of the outer thread of the inner body the degree of axial displacement or axial flexing of the blocking member's free end can be modified and controlled.

According to another embodiment the blocking member comprises an abutment at its free end section facing in an axial direction to axially abut with a corresponding abutment of the dose member. Typically, the abutment of the blocking member may face in the proximal direction so as to axially abut with a correspondingly-shaped distally facing abutment of the dose member. The distal abutment of the dose member may coincide with a distal end of the dose member. It is also conceivable that the dose member and the display member are arranged in a somewhat convoluted or nested way.

In typical embodiments the dose setting position of the dose member coincides with a proximal end position of the dose member relative to the display member. Depressing the dose member in the distal direction advances the dose member into the dose dispensing position. In such embodiments the abutment of the blocking member typically faces in the proximal direction. When the blocking member is in the release position there may exist a small axial gap between the abutment of the blocking member and the corresponding abutment of the dose member. In the release position, the dose member is free to be displaced in the distal direction to arrive in the dose dispensing position relative to the display member. Alternatively, when in release configuration, the blocking member may also be in axial abutment with the dose member. Blocking member and blocking structure may then be disengaged. To summarize, when in release configuration, the dose member is distally displaceable relative to the housing.

The blocking member does not necessarily have to conduct a displacement or a flexing motion in the axial direction as it engages with the blocking structure of the inner body's elongated shaft. It is also conceivable, that when blocking member and blocking structure are in mutual engagement the blocking member remains non-flexed but is inhibited to flex in the distal direction. In such an embodiment the blocking member may be even in permanent axial engagement with the abutment of the dose member. When in a release position the blocking member is then still in axial abutment with the dose member but due to a release from the blocking structure the blocking member is then free to flex or to pivot in distal direction so that the dose member is axially displaceable to initiate dispensing of a dose.

When in blocking configuration, the dose member is axially engaged and is in axial abutment with the blocking member being further in axial abutment with the blocking structure. In this way, any distally directed force exerted on the dose member is counteracted and transferred to the blocking structure and hence to the housing.

In a further embodiment the axial position of a distal end of the blocking structure on the inner body defines a maximum size of a dose for a priming procedure. As long as the blocking member is axially separated from the blocking structure and as long as the blocking member is located distally from the distal end of the blocking structure it remains in the release position. This is typically the case when the display member and hence the entire drive mechanism is in a zero set dose configuration or when only a small dose is set, such as 2 IU that is typically dispensed to conduct a priming procedure. When a dose is set that exceeds this lower threshold coinciding with the maximum size of a dose for a priming procedure, the blocking member engages with the blocking structure. It is then either prevented from flexing in the distal direction or it is actually flexed slightly in the proximal direction so as to block a distally directed dispensing displacement of the dose member.

In a further embodiment the axial position of a proximal end of the blocking structure on the elongated shaft of the inner body defines a minimum size of a therapeutic dose. The above mentioned blocking of the dose member remains until the display member is dialed further so to disengage and to liberate the blocking member. As the display member is dialed above such a maximum threshold coinciding with the minimum size of a therapeutic dose, the engagement of blocking member and blocking structure is released so that the dose member is no longer prevented from displacement in the distal direction. Once a therapeutic dose of a desired size exceeding the predefined minimum size has been set, the drive mechanism is operable to start a dispensing procedure.

According to a further embodiment a distal end of the blocking structure or blocking thread is chamfered. In this way the blocking member, in particular its radially inwardly extending protrusion directly mechanically engaging with the blocking thread becomes subject to a small axial displacement in accordance to the angle of the chamfered distal end of the blocking thread as the blocking member and the blocking thread mutually engage during setting of a dose.

By means of the chamfered distal end, a smooth and reliable engagement of the blocking member with the blocking thread can be achieved when the radially inwardly extending protrusion of the blocking member passes over the end of the blocking thread. Similar to the distal end, the proximal end of the blocking thread can also be chamfered in order to provide a smooth and reliable engagement with the blocking member when dialing down or in dose decrementing direction to cancel selection of a dose.

In a further embodiment and when rotating the display member in a dose incrementing direction the protrusion of the blocking member slides over the chamfer of the blocking thread's distal end to flex the blocking member's free end section from its release position towards its blocking position. Alternatively, the protrusion slides over the chamfer to axially abut with the blocking thread's proximally facing edge. As the protrusion of the blocking member passes the chamfered end of the blocking thread it slides along a proximally facing edge of the blocking thread and therefore remains in axial abutment with the blocking thread, thereby preventing a distally directed displacement of the blocking member relative to the blocking thread. In one embodiment, the blocking member remains flexed and remains in axial abutment in the proximal direction with the blocking thread since the blocking thread and the outer thread of the inner body's elongated shaft have the same lead.

In this way, the blocking member is axially supported by the proximal edge of the blocking thread as long as the blocking member is engaged with the blocking thread. Any axial and distally directed forces acting on the blocking member, e.g. induced by the dose member, are directly supported and transferred to the blocking thread and hence to the inner body. In this way, a rather direct axial force transfer between the dose member and the inner body can be provided, leading to a rather intuitive and direct mechanical feedback to a user, that the distally directed displacement of the dose member is actually blocked.

The location of the axial support provided to the blocking member by the proximally facing edge of the blocking thread in the blocked condition is also beneficial in that the flexible part of the blocking member does not have to withstand or to counteract large axial forces. Consequently, the blocking member can be designed with a thin or fine structure so that a desired degree of flexibility can be achieved for a low dispensing force.

When the blocking member is located proximally from the proximal end of the blocking thread a dose may be dispensed, since the blocking member is then no longer axially engaged with the blocking structure. To dispense a dose the dose member is displaced axially in the distal direction, which in turn flexes the blocking member in the distal direction, permitting the clutch between the dose member and display member to release. When the clutch has released the protrusion of the blocking member may slide distally beyond a distally facing edge of the blocking thread as the blocking member passes the proximal end of the blocking thread in distal direction when the display member is rotates in a dose decrementing direction during dose delivery.

During delivery of a dose the geometric shape and design of the blocking member and the blocking structure is such that the radially inwardly extending protrusion of the free end section of the blocking member slides along a distally facing edge of the blocking thread. The protrusion does not necessarily have to slide along the distal edge. It may beneficially be separated distally from the distal facing edge of the blocking structure. However, it is axially separated from a proximal edge of the blocking thread. At the beginning of a dose dispensing procedure the blocking member is subject to a distally directed displacement or distally directed pivoting under the action of the distally advancing dose member. Then, the radially inwardly extending protrusion of the blocking member slides along the distally facing edge of the blocking thread but does not engage with its proximally facing edge.

During dose dispensing the blocking member, in particular its radially inwardly extending protrusion will pass the proximal end of the blocking structure of the inner body in a distal direction. In the event that the dose member is then released to abruptly interrupt the dispensing procedure the protrusion of the blocking member may axially abut with the distally facing edge of the blocking thread. If the dose member is released the blocking member cannot flex back proximally because it is constrained by the blocking thread. Thus when the dose member is pressed distally again, dispense can continue.

In another embodiment the display member comprises a number sleeve and a dial sleeve. The at least one blocking member is located on the dial sleeve or the at least one blocking member is integrally formed with the dial sleeve. Typically, the number sleeve and the dial sleeve are permanently rotationally and axially locked to each other. It is typically the number sleeve of the display member that is threadedly engaged with the outer thread of the inner body.

The dividing of the display member in two separate components, a number sleeve and a dial sleeve is beneficial for injection molding of the individual components and for their assembly in the drive mechanism. The number sleeve is that part of the display member that is provided with consecutive numbers or symbols on its outer circumference indicating a size of a dose actually set. Depending on the helical motion or position with regards to the outer thread of the inner body respective numbers on the number sleeve show up in the aperture of the window in the outer body of the housing of the injection device.

The dial sleeve may be a different color to the number sleeve. Moreover it may be manufactured or composed of a different injection moldable plastic material compared to the number sleeve. So the at least one blocking member or all blocking members of the blocking mechanism may be located or integrally formed on or with the dial sleeve. Because the dial sleeve does not need to be printed or coated with dose indicating numbers or indicia, more material choices are available.

For instance, the dial sleeve and hence the at least one blocking member attached thereto or integrally formed therewith could be made of a plastic material such as polyoxymethylene (POM). Such a plastic material is difficult to print but offers desirable mechanical properties in terms of durability, flexibility and stability, in particular with regard to the at least one blocking member. So by separating the display member into two separate sleeves, a number sleeve and a dial sleeve and by providing the at least one or all blocking members on the dial sleeve an optimized plastic material can be chosen for the manufacturing of the dial sleeve and its blocking members. This plastic material that does not need to fulfill any printing requirements or restrictions and may be mechanically optimized with regards to the mechanical demands and requirements of the at least one blocking member.

According to another embodiment the inner body may comprise a first and optionally a second maximum dose stop at its outer circumference to engage with first and second radially inwardly extending maximum dose stops of the display member, respectively. First and optionally also second maximum dose stops of the inner body and the display member mutually and simultaneously engage when the display member arrives in a maximum dose position. The maximum dose position limits the amount of medicament that is to be injected by a single dose dispensing action. Typically, the maximum dose size may be limited to e.g. 60 IU, 80 IU, 120 IU. Mutually corresponding maximum dose stops of the inner body and the display member typically extend axially and radially. In this way tangentially facing stop faces mutually engage and mutually abut as soon as the maximum dose position has been reached.

Providing two pairs of maximum dose stops that are axially separated provides an improved and well-defined stop functionality. In this way, stop forces to inhibit a rotation of the dose member past a maximum dose configuration can be split to the two axially separated pairs of dose stops. Consequently, the overall design of the dose stops, in particular their dimensions can be reduced. Also the mechanical load between the mutually engaging dose stops of the display member and inner body is reduced compared to embodiments making use of only one pair of dose stops.

According to a further embodiment a maximum dose stop of the display member facing in a tangential direction is located on the free end section of the blocking member. The abutment at the free end section of the blocking member may face in the proximal direction so that the flexible arm of the blocking member somehow comprises an L-shaped structure. It is generally conceivable that the maximum dose stop of the display member, in particular a proximally located maximum dose stop of the display member is located on the free end section of the blocking member. Typically, this maximum dose stop faces towards the base portion of the blocking member's flexible arm where the flexible arm joins the display member. In this way the flexible arm is subject to a tangentially directed tensile force as its maximum stop engages with a correspondingly-shaped maximum stop of the inner body. The tensile force extends substantially parallel to the L-shaped elongation of the flexible arm. Any stop forces or torques to be transmitted between the flexible arm and the maximum dose stop of the display member do not harm the mechanical integrity of the flexible arm. Thanks to the orientation and position of the flexible arm's stop face the arm can be designed as a comparatively thin and flexible structure while being able to transmit rather large forces and/or torques in tension.

In a further embodiment the blocking thread comprises at least one recess, interruption or gap having a size to receive the blocking member and/or its radially inwardly extending protrusion. In this way the drive mechanism is configurable as a fixed dose drive mechanism, by way of which only one or several doses of a pre-determined size can be dispensed. The circumferential or tangential size of the gap or gaps define the dose sizes that may be dispensed by the device. The tangential size of the at least one gap is at least as large as the blocking member or its radially inwardly extending protrusion that actually passes through the gap in the blocking thread when initiating a dose dispensing procedure. There may be several gaps tangentially and/or axially separated from each other along the blocking thread. Dose dispensing is then only possible when the tangential position of respective gap overlaps or axially coincides with the actual position of the blocking member or its protrusion.

With the present disclosure and simply by the specific design and geometry of the blocking structure or blocking thread the drive mechanism can be configured to only allow setting and dispensing of doses of a specific or discrete size.

According to a further embodiment the drive mechanism comprises a piston rod and a tubular-shaped driver, both extending in the axial direction. The piston rod typically comprises a first outer thread engaged with an inner thread of the inner body. In this way, a rotation of the piston rod in a dispensing direction leads to a distally directed advancing of the piston rod relative to the inner body and hence relative to the cartridge axially constrained inside the housing of the injection device. Moreover, the piston rod comprises a second outer thread of opposite hand compared to the first outer thread, wherein the second outer thread is threadedly engaged with an inner thread of the driver. In this way, an axial but non-rotative displacement of the driver in the distal direction induces a rotation of the piston rod which due to the threaded engagement with the inner thread of the inner body advances it in the distal direction during dose dispensing. Hence, during dose dispensing the driver is subject to a distally directed purely translational but non-rotational movement. For dose dispensing the driver is typically rotationally locked to the inner body. It may be coupled to splines in the inner body so that the driver is preventing from rotating relative to the body but is free to be axially displaced relative to the body during dose dispensing.

In a dose setting configuration the driver may be rotationally locked or rotationally coupled to the display member so as to follow the helical motion of the display member relative to the inner body. In dose setting mode, a splined engagement of driver and inner body is abrogated or released. Instead, the driver is free to rotate in accordance to a helical path that coincides with the threaded engagement of driver and piston rod so that the driver is axially displaceable in the proximal direction relative to the inner body and relative to the piston rod, which during dose setting is stationary with regard to the inner body.

By means of the two threads of the piston rod of opposite hand a displacement transition ratio between the distally directed displacement of the driver and the piston rod can be implemented. A rather large axial displacement requiring a rather low dispensing force can therefore be transferred into a rather short displacement of the piston rod with a rather large dispensing force.

According to another embodiment the dose member is permanently splined with the driver. The driver in turn is selectively rotationally lockable to the inner body by displacing the dose member into the dose dispensing position. When the dose member is in dose setting position the driver is no longer rotationally locked to the body but is free to rotate relative to the body, e.g. by means of a ratchet or clicker detent engagement by way of which the rotation of the driver relative to the body produces an audible and tactile click sound thereby indicating to the user, that subsequent discrete steps of dose setting actually take place.

The driver and the display member may be axially engaged either directly or indirectly via axial engagement of the dose member with both the driver and with the display member.

According to another embodiment the dose member and the display member are selectively rotationally lockable and releasable via a clutch. The clutch rotationally engages the dose member and the display member when the dose member is in dose setting position. Hence, in dose setting position a rotation of the dose member equally transfers to a respective rotation of the display member. Typically, the dose member or at least a portion thereof proximally protrudes from the proximal end of the display member. Rotation of the dose member in a dose incrementing direction simultaneously displaces the dose member and the display member in the proximal direction to proximally extend from the inner body or from the housing of the injection device.

The clutch between display member and dose member is released when the dose member is switched or depressed into its dispensing position. In the dispensing position or dispensing configuration the dose member is axially distally displaceable in a non-rotative way relative to the inner body. Simultaneously, the dose member, the driver and the display member are axially engaged. A depression of the dose member or exertion of a distally directed dispensing force onto the dose member therefore leads to a distally directed helical twisting motion of the display member together with a distally directed translation of the driver to induce a driving torque to the piston rod.

The dose member and the driver are permanently rotationally locked. For instance, the dose member and driver may be splined together so that the dose member is prevented from rotating during dose dispensing by the driver being rotationally locked to the inner body.

In another aspect the disclosure further relates to an injection device for setting and dispensing of a dose of a medicament. The injection device is typically configured as a pen-type injector. It comprises an elongated housing accommodating and receiving a drive mechanism as described above and a cartridge arranged inside the housing and filled with a liquid medicament. The cartridge is typically located and accommodated by a cartridge holder forming a distal portion of the housing of the injection device. When the injection device is implemented as a disposable device the cartridge holder and the proximal housing component are typically permanently interconnected. When implemented as a reusable device the cartridge holder is releasably connected with the proximal housing part so as to provide access to the cartridge for cartridge replacement as well as to enable a reset operation of the drive mechanism.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, embodiments of the drive mechanism and the injection device are described in detail by making reference to the drawings, in which.

DETAILED DESCRIPTION

Figure 1:
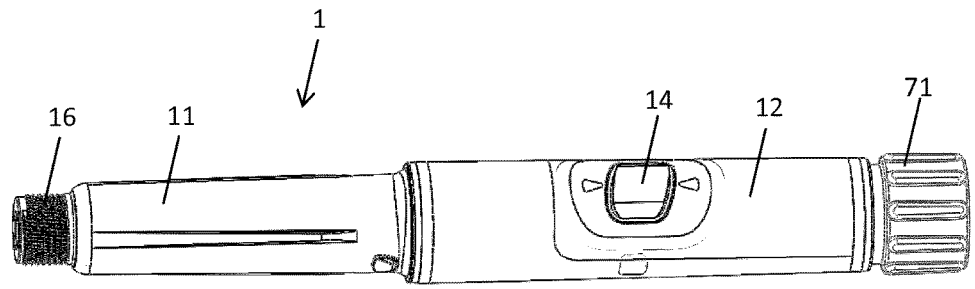
FIG. 1 shows a perspective outer view of the injection device.
Figure 13:
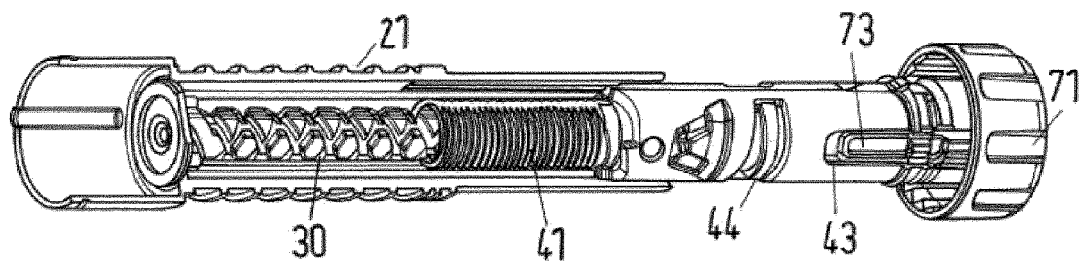
FIG. 13 shows the drive mechanism according to FIG. 12 in a maximum set dose configuration.
Figure 14:
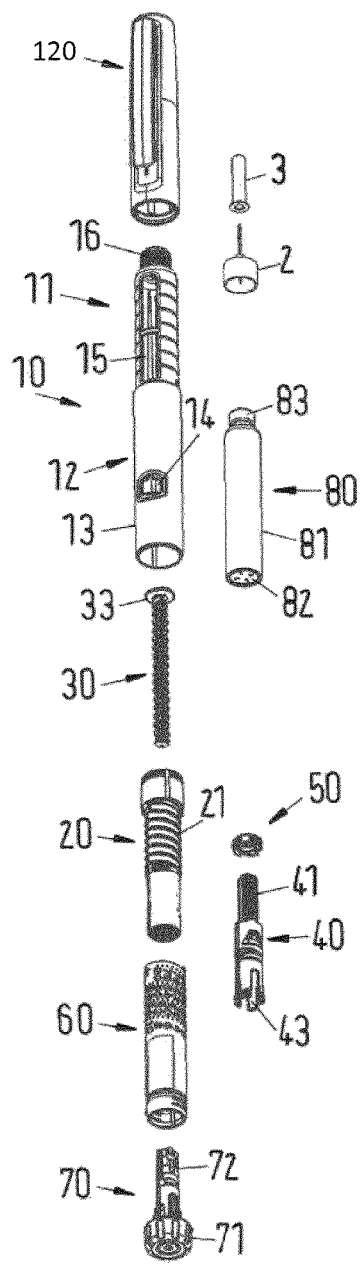
FIG. 14 is an exploded view of the components of the drive mechanism according to FIGS. 12 and 13.
Figure 15:
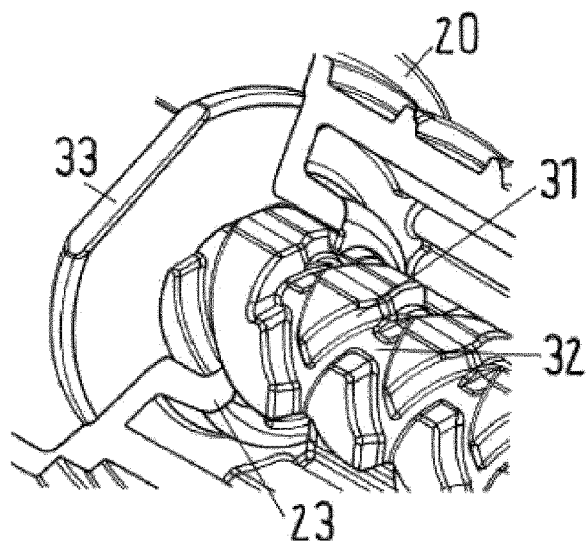
FIG. 15 is a perspective and cut view of the interface between inner body and piston rod.

FIG. 1 shows a drug delivery device 1 in the form of an injection pen. The device has a distal end, shown as left end in FIG. 1 and a proximal end located at the right hand side FIG. 1. The components or parts of the drug delivery device 1 are shown in FIG. 14 in more detail but without showing the blocking member or blocking structure. The drug delivery device 1 comprises an outer housing part 10, an inner body 20, a piston rod 30, a driver 40, a last dose nut 50, a display member 60, a dose member 70, a cartridge 80 and a cap 120, i.e. in total nine separate component parts. As shown in FIG. 14, a needle arrangement comprising a needle hub 2 and a needle cover 3 may be provided as additional components, which can be exchanged. The general concept and structure of the drive mechanism as shown in FIGS. 12 to 26 is similar to the mechanism disclosed in WO 2014/033197 A1, which is incorporated herein by reference.

The outer housing part 10 is a generally tubular element having a distal part, which forms a cartridge holder 11 for receiving the cartridge 80, and a proximal part, which forms an outer body 12. In one embodiment, the outer housing part 10 is transparent, with the outer body 12 being provided with an opaque layer 13. In FIG. 14, the opaque layer 13 covers most of the outer body 12 with the exception of a transparent window 14. Apertures 15 may be provided in the cartridge holder 11. Further, at its distal end the cartridge holder 11 has a thread 16 or the like for attaching the needle hub 2.

Figure 21:
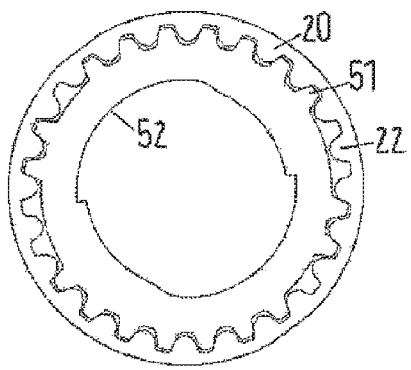
FIG. 21 is a cross section through the interface of last dose nut and inner body.

The inner body 20 is a generally tubular element having different diameter regions. The inner body 20 is received in the outer body 12 and permanently fixed therein to prevent any relative movement of the inner body 20 with respect to the outer body 12. An external thread 21 is provided on the outer surface of a shaft portion 20a of the inner body 20. Further, splines 22 are provided on the inner surface of the inner body 20 which are shown in FIG. 21. As can be taken from FIG. 15, the inner body 20 has near its distal end an inner thread 23.

The piston rod 30 is an elongated element having two external threads 31, 32 with opposite hand which overlap each other. One of these threads 31 engages the inner thread 23 of the inner body 20. A disk-like bearing 33 is provided at the distal end of the piston rod 30. As shown in FIG. 14, the bearing 33 may be attached to the piston rod 30 as a one-piece component via a predetermined breaking point. This allows that the bearing 33 is separated from the piston rod 30 such that the bearing 33 remains seated on the distal end of the piston rod 30 to allow relative rotation between the bearing 33 and the piston rod 30.

Figure 12:
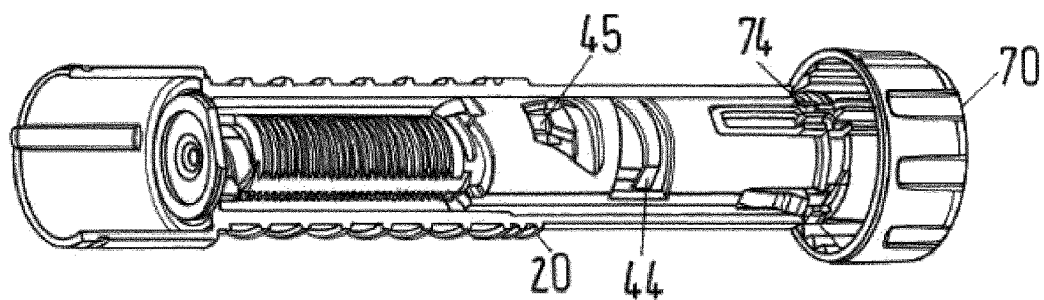
FIG. 12 shows a first embodiment of the drive mechanism in an initial configuration.
Figure 18:
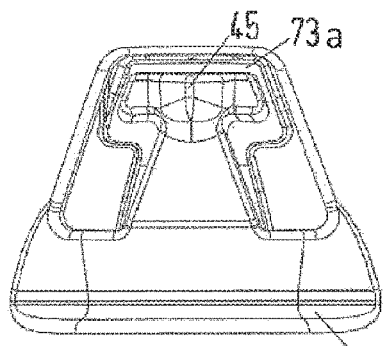
FIG. 18 is illustrative of a ratchet-like protrusion of the driver coinciding with a correspondingly-shaped receptacle on the outer circumference of the dose member.
Figure 19:
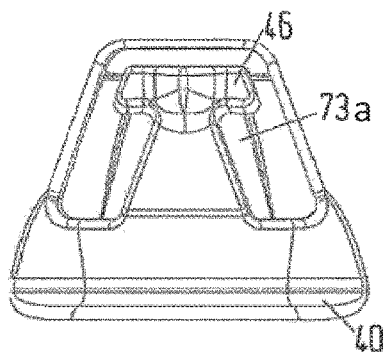
FIG. 19 is indicative of the configuration of FIG. 18 but with dose member and driver axially shifted.
Figure 22:
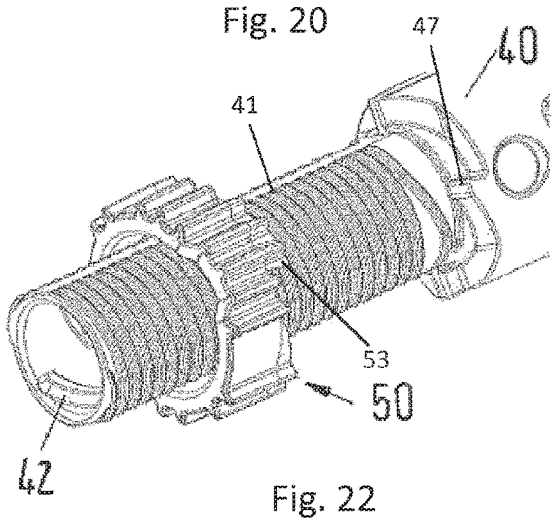
FIG. 22 shows the last dose nut threadedly engaged with a threaded portion of the driver.

The driver 40 is a generally tubular element having different diameter regions. A distal region of the driver 40 has an external thread 41. An inner surface of the driver 40 has an inner thread 42 as shown in FIG. 22 engaging one of the external threads 32 of the piston rod 30. The driver 40 surrounds the piston rod 30 and is at least partly located within inner body 20. The driver 40 has at least one proximal opening 43 or slit which will be explained in more detail below. Further, a resilient finger 44 is provided on the driver 40 by a U-shaped cut in the skirt of the driver 40 as shown in FIGS. 12 and 13. The finger 44 is allowed to flex in the axial direction and engages the dose member 70. In addition, a flexibly hinged protrusion 45 as shown in FIGS. 18 and 19, is provided on the driver 40 by a similar cut out in the skirt of the driver 40. The protrusion 45 is allowed to flex radially inwardly and is provided with lateral flaps 46. The protrusion 45 engages splines 22 of the inner body 20.

Figure 20:
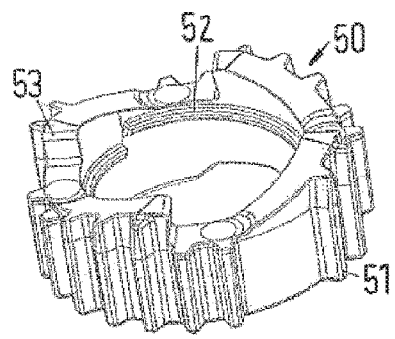
FIG. 20 shows an isolated perspective view of a last dose nut.

The last dose nut 50 is provided between the inner body 20 and the driver 40. External ribs 51 of the nut 50 engage splines 22 of the inner body 20. An internal thread 52 of the nut as shown in FIG. 20 engages the external thread 41 of the driver 40. As an alternative, splines and ribs could be provided on the interface between the nut 50 and the driver 40 and threads could be provided on the interface between the nut 50 and the inner body 20. As a further alternative, the nut 50 may be designed as e.g. a half nut. Further, in the embodiment of FIG. 20, four rotational hard stops 53 are provided on nut 50 for interaction with corresponding stops 47 on the driver 40 at the proximal end of the thread 41

The display member 60 is a generally tubular element with an internal thread 61 engaging the external thread 21 of the inner body 20. Thus, the display member 60 is interposed between the inner body 20 and the outer body 12. A series of numbers is provided, e.g. printed, on the outer surface of the display member 60. The numbers are arranged on a helical line such that only one number or only a few numbers are visible in through window 14 of the outer body 12. As will be explained in more detail below, the display member 60 is attached to the driver 40 preventing relative axial movement but allowing relative rotation.

Figure 11:
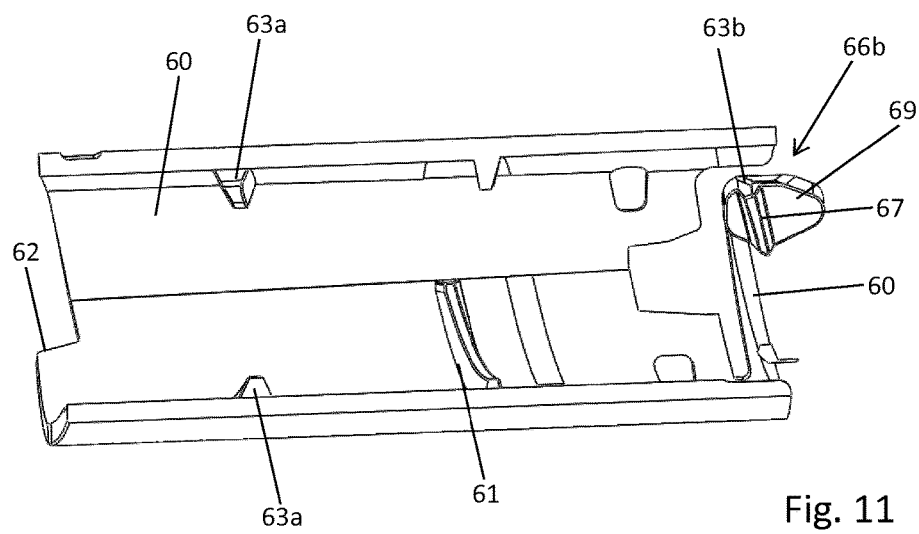
FIG. 11 is a perspective cut view of the interior of the display member.

A zero unit rotational hard stop formed by a stop wall 62 of the display member 60 and a corresponding stop face 24 on the inner body 20 as shown in FIGS. 3 and 11. FIGS. 3 and 11 show also a maximum dose (e.g. a 80 units) rotational hard stop formed by a stops 63a and 63b at the distal end and proximal ends of the display member 60 and a corresponding stops 25a, 25b on the outer circumference or in thread 21 of the inner body 20. Thus, a user is prevented from dialing below zero units and above e.g. 80 units.

The dose member 70 has a proximal end with an, e.g. serrated, flange or dose button 71 or outer skirt allowing a user to easily grip and dial the dose member 70. A sleeve-like part 72 of the dose member 70 with a reduced diameter extends in the distal direction 4 and is inserted into the driver 40 such that a limited relative axial movement is allowed but relative rotation is prevented. This is achieved by a rib 73 on the sleeve-like part 72 which is guided in a proximal opening 43 of the driver 40 as shown in FIG. 13. A recess 73a which generally has the outline of the protrusion 45 and its lateral flaps 46 is provided in the sleeve-like part 72 of dose member 70.

Figure 23:
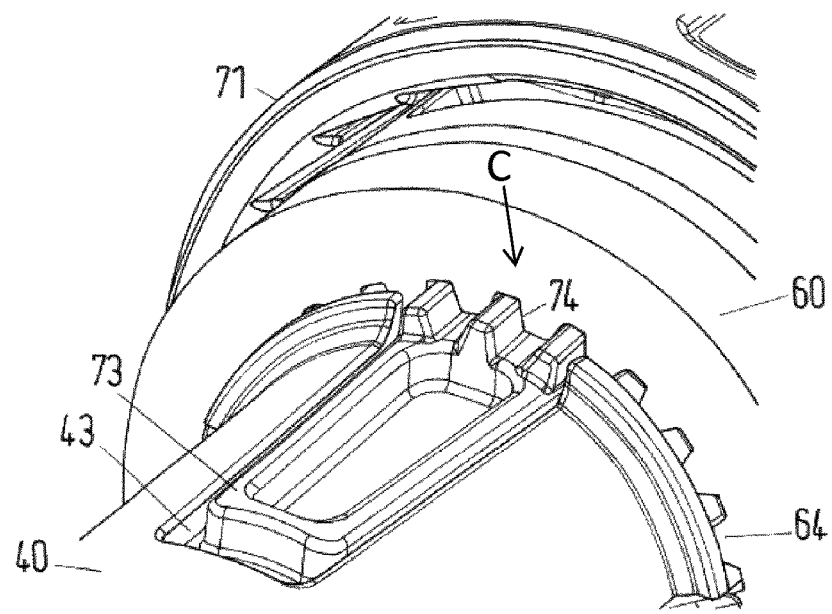
FIG. 23 shows the clutch between display member and dose member in engagement.
Figure 24:
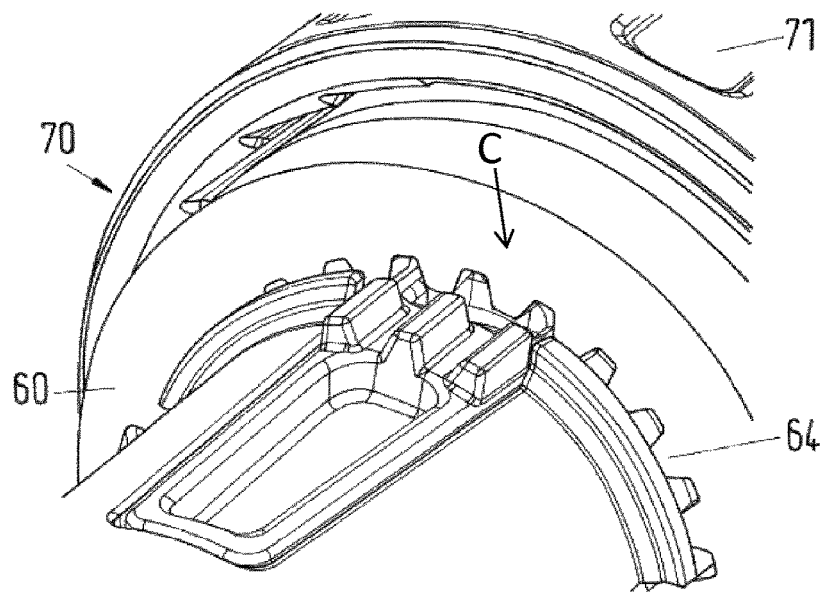
FIG. 24 shows the clutch according to FIG. 23 in a released configuration.

A clutch C is provided between the display member 60 and the dose member 70 by corresponding teeth 64 and 74 as shown in FIGS. 23 and 24. If the teeth 74 of the dose member 70 engage teeth 64 of the display member 60, these components will be rotationally locked. The resilient finger 44 of the driver 40 biases the dose member 70 in the proximal direction 5 of the device 1, i.e. in a direction engaging the clutch teeth 64, 74. The clutch C can be released allowing relative rotation by shifting the dose member 70 axially with respect to the display member 60 against the bias of finger 44.

Figure 25:
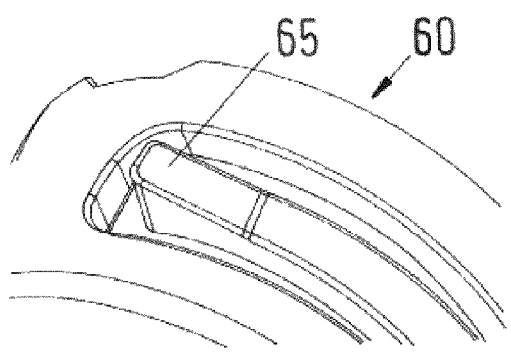
FIG. 25 shows a flexible arm of the display member to engage with a toothed profile of the dose member.
Figure 26:
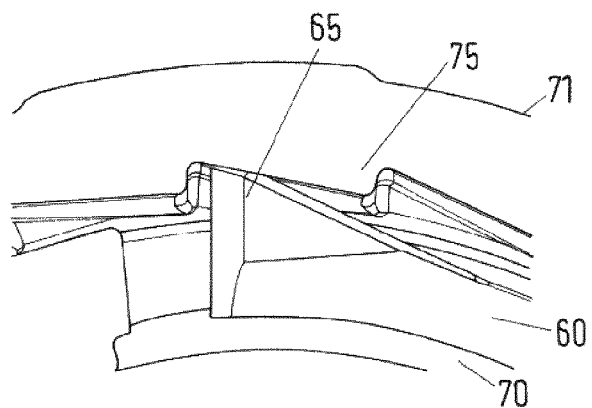
FIG. 26 shows the mutual engagement of the flexible arm with the toothed profile.
Figure 27:
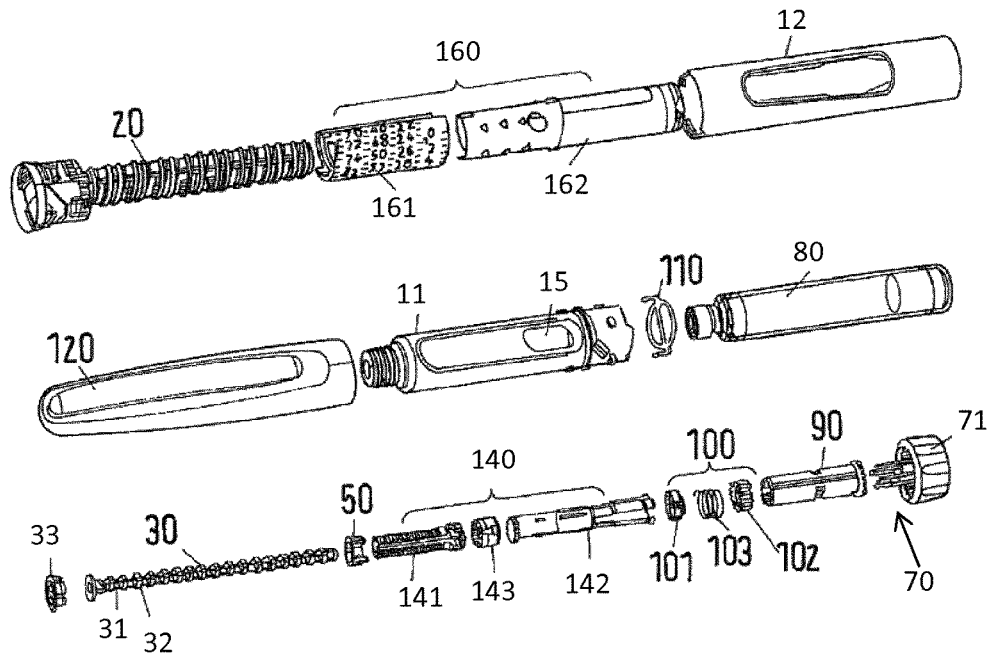
FIG. 27 shows an exploded view of another embodiment of the injection device which is of reusable type.
Figure 28:
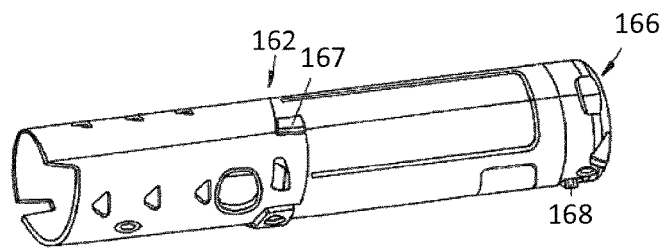
FIG. 28 shows a dial sleeve of the display member according to FIG. 27.

Further, a dispense clicker is provided by flexible arms 65 on the display member 60 and a toothed profile 75 on the inner side of the dose button 71 of the dose member 70. This clicker is shown in FIGS. 25 and 26.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal cap 83 is used to hold the rubber seal in place. The cartridge 80 is provided within the cartridge holder 11 with bearing 33 of piston rod 30 abutting bung 82.

FIG. 14 shows the cap 120 attached to the distal end of the device 1, thus covering the cartridge holder 11. The cap 120 may be releasable snapped onto the outer housing 10 and can be taken off for use of the device 1.

In the following, the function of the disposable drug delivery device 1 and its components will be explained in more detail.

To use the device, a user has to select a dose. In the start (at rest) condition as shown in FIGS. 1 and 12 the display member 60 indicates the number of doses dialed to the user. The number of dialed units can be viewed through the dose window 14 in the outer body 12. Due to the threaded engagement between the display member 60 and the inner body 20 rotation of the dose member 70 in a clockwise fashion causes the display member 60 to wind out of the device and incrementally display the number of units to be delivered.

During dose setting dose member 70, driver 40 and display member 60 are rotationally locked together via clutch teeth 64, 74. Further, dose member 70, driver 40 and display member 60 are axially coupled. Thus, these three components wind out of the outer housing 10 during dose setting.

Figure 16:
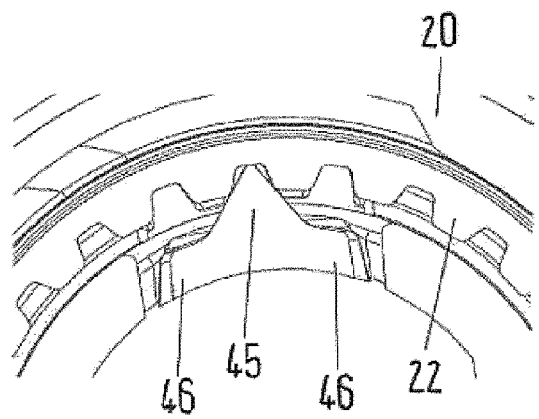
FIG. 16 shows a cross section through the interface between driver and inner body.
Figure 17:
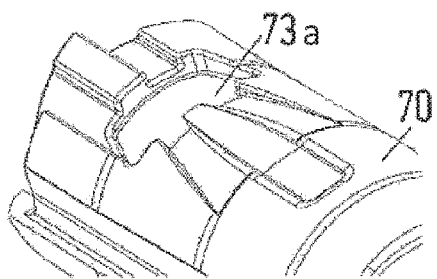
FIG. 17 is a perspective view of the outer circumference of a shaft portion of the dose member.

Clockwise rotation of the dose member 70 causes the driver 40 to rotate and in doing so it advances along the piston rod 30 which remains fixed throughout dialing. The protrusion 45 and splines 22 form a clicker arrangement that provides tactile and audible feedback to the user when dialing doses. This clicker arrangement has the further functions of defining discrete positions for the display member 60 when dialing and of providing a method of locking the rotation of the driver 40 and the dose member 70 when dosing. During dialing hence, during dose setting the dose member 70 is in an axial position relative to the driver 40 such that the pocket or recess 73a is located radially inwards of the protrusion 45. Thus, the protrusion 45 is allowed to flex radially inwards to overcome splines 22 thereby providing a tactile and audible feedback to the user. FIG. 16 shows the flexible protrusion arm 45 located between splines 22 which are e.g. 15° apart.

At the maximum settable dose of 80 units, the stop features 63a, 63b and 25a, 25b shown in FIGS. 3 and 11 engage to prevent further dialing. The last dose nut 50 provides the function of logging the total number of dispensed units. The nut 50 locks the device 1 at the end of life and as such no more drug can be dialed or dispensed by the user. The last dose nut 50 and the driver 40 are connected via a threaded interface 41, 52 as explained above. Further, the last dose nut 50 is assembled into splines 22 as shown in FIG. 21 such that the nut 50 and the inner body 20 are permanently rotationally locked together. Rotation of the driver 40 during dialing causes the nut 50 to advance along the driver 40 thread 41. The nut 50 is free to slide axially within the inner body 20 at all times which allows advancement of the nut 50. The change in pitch shown in FIG. 22 towards the final doses axially accelerates the advancement of the nut 50 towards the end of life lockout condition.

At the end of life condition, the stop features 53 of the last dose nut 50 contact the corresponding features 47 on the driver 40. The splined contact with inner body 20 reacts any torque transmitted by these stop features 47.

With the desired dose is dialed, the device 1 is ready for dose dispensing. This basically requires pushing the dose member 70 which will result in a disengagement of the clutch teeth 64, 74. As mentioned above, when dialing a dose the dose member 70 is 'biased out' and the clutch features 64, 74 which rotationally lock the driver 40, dose member 70 and display member 60 together are engaged as shown in FIG. 23. Upon pressing the proximal button portion of the dose member 70 the clutch features 64, 74 disengage as shown in FIG. 24 and a relative rotation between the display member 60 and the dose member 70 is possible. In all conditions the driver 40 and the dose member 70 are rotationally locked together by the engagement of the rib 73 and the opening 43. Thus, with the clutch 64, 74 disengaged, i.e. dose member 70 depressed or pushed in distal direction the dose member 70 and the driver 40 are rotationally locked together with the dose member 70, the driver 40 and the display member 60 still being axially coupled.

At the same time the relative axial movement of the dose member 70 with respect to the driver 40 results in the pocket or recess 73 being shifted relative to the protrusion 45. Thus, the protrusion 45 is prevented from flexing inwards because flaps 46 rest on a non-recessed area of the sleeve portion 70a of the dose member 70. A comparison of FIGS. 18 and 19 shows this activation of the lockout feature preventing the flexible protrusion arm 45 from overcoming splines 22 if the dose member 70 is pressed. In this condition, the driver 40 and the dose member 70 are rotationally constrained to the inner body 20 thus preventing any rotation relative to the outer housing 10 if the splines 22 are axially aligned with the device as shown in FIG. 16. There is also conceivable an alternative embodiment with twisted splines 22. There, the twisted splines serve to induce a rotation of the driver as it is subject to a distally directed displacement during dose dispensing.

With the desired dose dialed the dose member 70 can be depressed and the piston rod 30 driven forward to dispense drug from the cartridge 80. The interaction of mating threads between the piston rod 30, driver 40 and inner body 20 delivers a mechanical advantage, for example of 2:1 in the illustrated example. The initial and new device in a zero dose configuration is depicted in FIG. 12 while FIG. 13 shows the device 1 with 80 units dialed prior to pushing the dose member 70.

During dose dispensing a dispense clicker is active which involves dose member 70 and display member 60. The dispense clicker provides primarily audible feedback to the user that drug is being dispensed. As shown in FIGS. 25 and 26 the interaction between the flexible arms 65 on the display member 60 and the toothed profile 75 on the button flange 71 provide this dispense click. Relative rotation is only allowed in one direction. This occurs when the components are decoupled during dispense and a click is produced for every unit.

Figure 2:
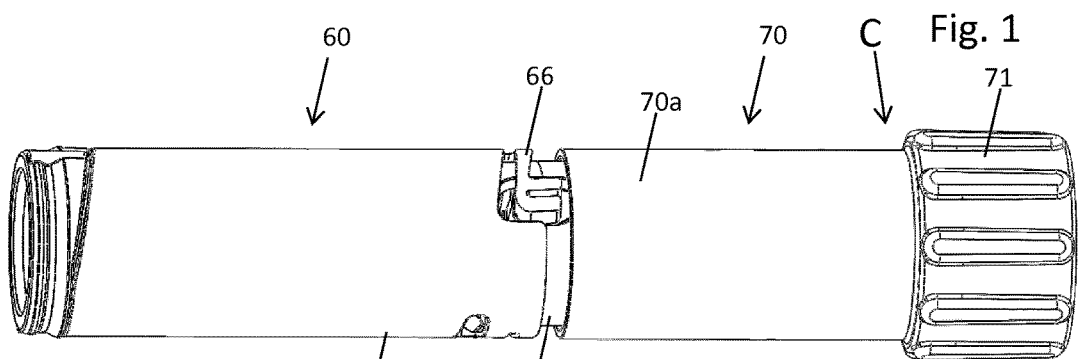
FIG. 2 shows an isolated and abstract illustration of display member and dose member.

In FIGS. 2-11 the minimum dose mechanism or the minimum dose function of the drive mechanism is explained in general. As it is apparent from a comparison of FIGS. 2 and 12, the shape of the dose member 70 as illustrated in FIG. 2 slightly varies from the overall shape of the dose member 70 as shown in the embodiment of FIGS. 12-26. However, the overall functionality of the dose member 70 and its interaction with all other components in particular with the display member 60 and the driver 40 is at least similar or even identical to the interaction as explained above in connection with FIGS. 12-26. In the illustrations according to FIGS. 2-11 the piston rod 30, the driver 40 as well as the last dose nut 50 are omitted for reasons of clarity.

Figure 3A:
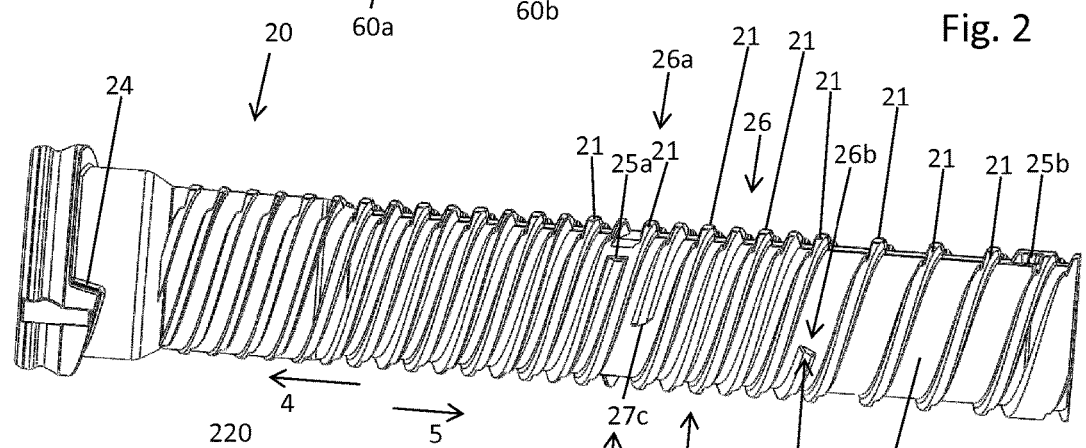
FIG. 3a is an isolated perspective view of the inner body.

The inner body 20 comprises an elongated shaft 20a as shown in FIG. 3. Along the outer circumference of the elongated shaft there is provided the outer thread 21 that is threadedly engaged with a radially inwardly extending thread feature or inner thread 61 of the display member 60 as shown in FIG. 11. In addition, the elongated shaft 20a comprises a blocking structure 26. In the present embodiment the blocking structure 26 comprises a blocking thread 27 extending axially between convolutions of the outer thread 21. The blocking structure 26, hence the blocking thread 27 terminates in distal direction 4 with a distal ends 26a, 27a. The blocking structure 26 terminates in proximal direction 5 with proximal ends 26b, 27b. Hence, the blocking thread 27 terminates in proximal terminal direction 5 with a proximal end 27b. As illustrated in FIG. 3a the distal and proximal ends 27a, 27b of the blocking thread 27 are located within the axial extension of the outer thread 21. The axial offset between the blocking thread 27 and the outer thread 21 is about half the pitch of the outer thread 21. The lead of the blocking thread 27 is substantially equal or absolutely identical to the lead of the outer thread 21.

As shown in FIG. 2 the display member 60 comprises a stepped down portion at its proximal part 60b which is received in the sleeve-shaped dose member 70 having a tubular shaft 70a extending from the dose dial or dose button 71 in distal direction 4. The proximal part 60b and the dose member 70 are selectively rotationally engageable by means of the clutch C as it is described in connection with FIGS. 23 and 24. The proximal part 60b of the display member 60 is not further illustrated in FIGS. 4-11 for reasons of simplicity.

Figure 4:
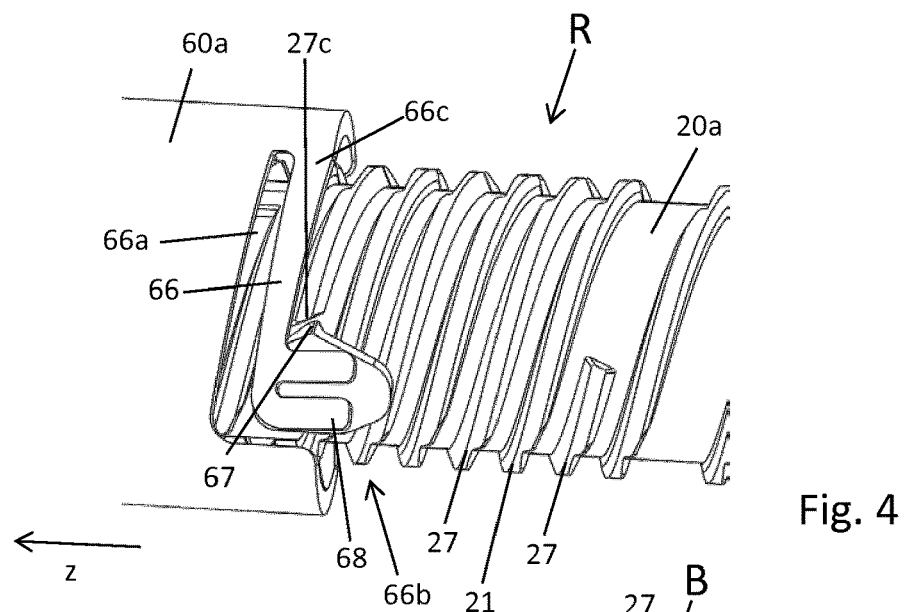
FIG. 4 shows the interaction of blocking member and blocking structure prior to engagement when setting a dose.
Figure 5:
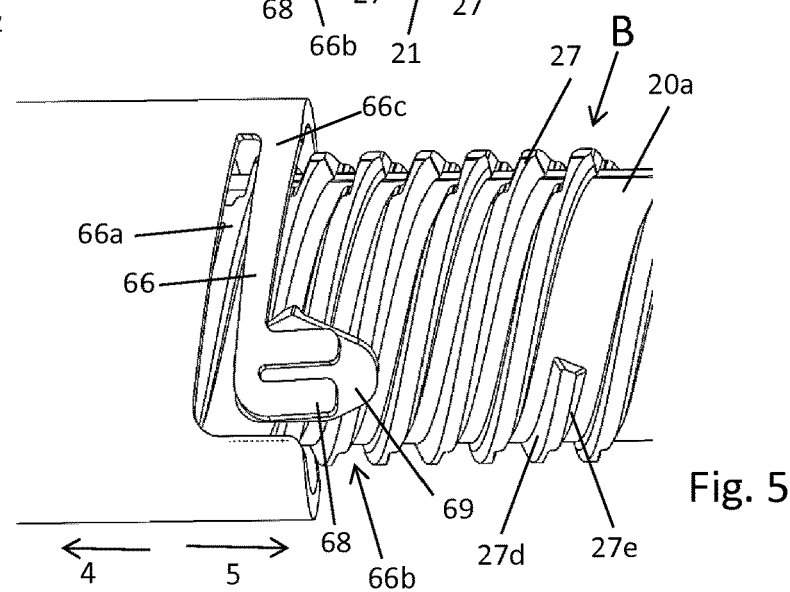
FIG. 5 shows the configuration according to FIG. 4 with the display member rotated further in the dose incrementing direction.

The display member 60 comprises at least one blocking member 66 as shown in FIG. 4. The blocking member 66 comprises a flexible arm extending in a tangential direction and coincides with the sidewall 60a of the display member 60 as seen in an axial projection. The blocking member 66 comprises a base portion 66c by way of which the blocking member 66 is joined with the sidewall 60a of the display member 60. Between the blocking member 66 and an axially adjacent sidewall portion 60a there is provided a tangential slit 66a or a respective gap by way of which the blocking member 66, in particular its free end 66b is free to flex or to deform in axial direction (z). Hence, the sidewall 60a of the display member 60 comprises a recess that is large enough to support and to allow distally or proximally directed flexing or displacing of the blocking member 66.

Figure 6:
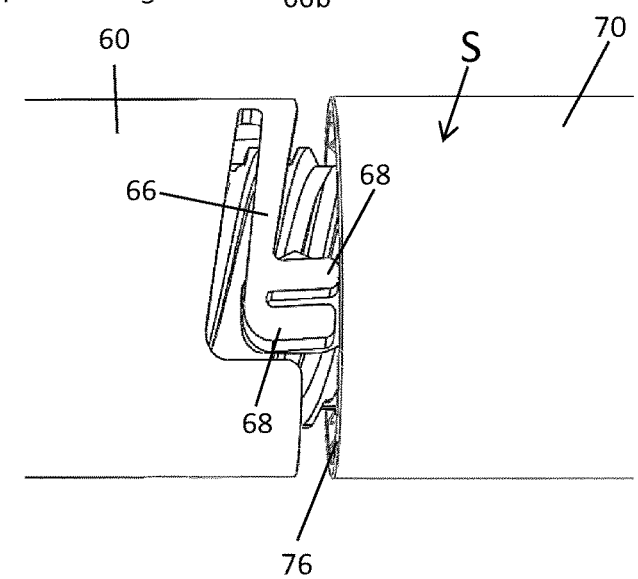
FIG. 6 shows the configuration according to FIG. 5 and the interaction of the blocking member with the dose member.

As shown in FIG. 11 the free end 66b of the blocking member 66 comprises a radially inwardly extending protrusion 67. The protrusion 67 has a rib-like shape and extends substantially parallel to the inner thread 61. The protrusion 67 is particularly adapted to mate or to engage with the blocking thread 27 on the outer circumference of the inner body 20. As can be seen from FIGS. 4 and 5 the blocking member 66 comprises an L-shaped structure with a long side extending tangentially and with a short side extending axially, in proximal direction. At the proximal end of the free end 66b of the blocking member 66 there are provided two fork-like abutment portions 68 that are adapted to axially engage with a distally facing abutment 76 of the dose member 70 as shown in FIG. 6. The abutments 68 are arranged radially outwardly of a support face 69 which extends proximally from the proximal end of the abutment portion 68. As shown in the various configurations of FIGS. 2 and 6 the support face 69 is constrained by an inside facing sidewall of the dose member 70 so as to provide an effective axial guiding between the mutually corresponding axial abutments 68, 76 of blocking member 66 and dose member 70.

The distal end 27a of the blocking thread 27 defines the maximum size of a 'priming' dose while the axial location of the proximal end 27b of the blocking thread 27 defines the minimum value of a dose that can be set and subsequently dispensed by the injection device 1. In an initial configuration, prior to setting a dose or when the drive mechanism is in a zero dose configuration the blocking member 66, in particular its protrusion 67 is not yet engaged with the blocking thread 27 as shown in FIG. 4. In this initial configuration the blocking member 66, in particular its protrusion 67 is located distally from the distal end 27a of the blocking thread 27. Hence, the dose member 70 is displaceable in distal direction to disengage the clutch C and to initiate a dispensing procedure as described above.

When the display member 70 is turned further in a dose incrementing direction relative to the inner body 20 the protrusion 67 of the blocking member 66 engages the chamfered distal end 27a of the blocking thread 27. Thanks to the chamfer 27c the protrusion 67 experiences a slight displacement in proximal direction 5, thereby pivoting the blocking member 66 with its free end in proximal direction 5. In this way, the axial size of the gap 66a at least in the region of the free end section 66b enlarges and the abutment 68 of the free end section 66b approaches the corresponding abutment 76 of the dose member 70. As the protrusion 67 has passed the chamfer 27c it is urged in proximal direction 5 by the proximally facing edge 27e of the blocking thread 27.

In this configuration the abutment 68 of the free end 66b of the blocking member 66 axially abuts with, or is in very close proximity to the abutment 76 of the dose member 70, thereby inhibiting and blocking a distally directed displacement of the dose member 70 relative to the inner body 20 as well as relative to the display member 60. In this way the clutch C remains locked and the device 1 cannot be switched into a dispensing mode. As long as the blocking member 66 is engaged with the blocking thread 27 or with the blocking structure 26 this axial abutment and blocking configuration between the blocking member 66 and the dose member 70 is maintained. Hence, the blocking member cannot flex because it is engaged with the blocking thread. Because the dose member is in abutment with the blocking member also the dose member cannot be displaced distally to initiate dispense.

When the flexible blocking member 66 is axially engaged with the proximally facing edge 27*e* of the blocking thread 27 any axially directed force transferred via the dose member 70 is directly transferred via the blocking member 66 to the inner body 20. Due to this comparatively short and rather direct load path between the dose member 70 and the inner body 20 a robust and strong blocking action can be provided. In this blocking configuration there is inherently only very little flexibility that could otherwise confuse a user. With the blocking member being in axial proximal abutment with the blocking thread 27 and being further in axial distal abutment or close proximity with the dose member 70, the blocking member is axially sandwiched between the dose member 70 and the inner body 20. In this way axial blocking of the dose member 70 is relatively free of play or slack that may confuse a user.

Figure 7:
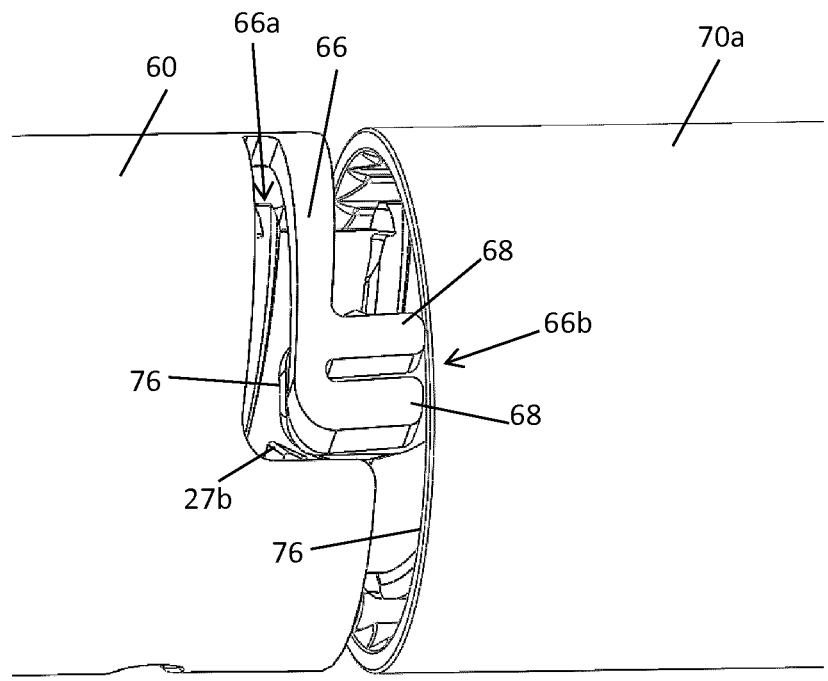
FIG. 7 is illustrative of a configuration wherein the blocking member disengages the blocking structure when a minimum size of a therapeutic dose has been set.

It is only when dialing the display member 60 further in the dose incrementing direction that the blocking member 66 disengages the blocking structure 26, i.e. the blocking thread 27, so that the blocking member 66 relaxes and returns to its unbiased and initial state as indicated in FIG. 7. There, the protrusion 67 has just passed the proximal end 27*b* of the blocking thread 27. Consequently, the blocking member 66, in particular its free end section 66*b* is displaceable or flexible in distal direction 4 either under the effect of a distally advancing dose member 70 or just by a relaxation into its natural unbiased state.

Figure 8:
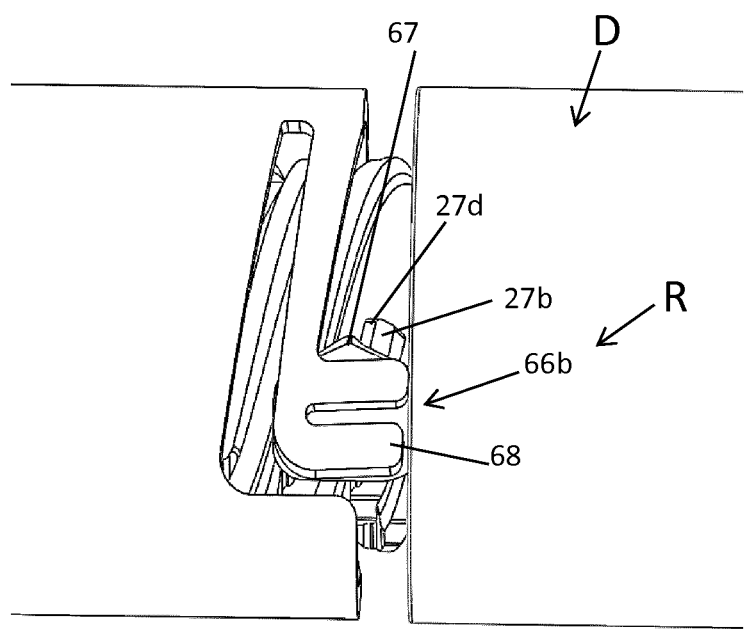
FIG. 8 shows the configuration of the device during dose dispensing.

In FIG. 8 a configuration is shown wherein the drive mechanism has dispensed a few units so that the residual amount of medicament to be dispensed is less than the intended minimum dose size. As the drive mechanism conducts a dose dispensing procedure the blocking member 66 is in its release position R and it is flexed in the distal direction due to the distally directed displacement of the dose member 70 being then in dose dispensing position D. As the display member 60 rotates in the dose decrementing direction during dose dispensing the blocking member 66 passes along the distal side of the blocking thread 27*d* as shown in FIG. 8.

When entering the blocking thread 27 from the proximal side during dose dispensing the protrusion 67 is located near a distally facing edge 27*d* of the blocking thread 27. Even in the event that in such a configuration as shown in FIG. 8 the dispensing procedure should be interrupted the blocking member 66 is effectively prevented from pivoting or flexing in the proximal direction 5. Therefore, in the event that the dose dispensing procedure should be continued the dose member 70 is not prevented by the blocking member from being displaced into its dose dispensing position D. Even if the blocking member 66 and the dose member come into in axial abutment prior to the dose member 70 reaching the dose dispensing position D the blocking member 66 is free to be at least slightly displaced in axial distal direction 4 and thus dispensing can be re-initiated.

In this condition, the clutch C between the dose member 70 and the display member 60 is opened or released and the dispensing can continue. In other words, the blocking member 66, in particular its free end section 66*b* remains trapped on the distal side of the blocking thread 27. The user is then able to resume dispensing a dose, even when the display member 60 should be in a position below the predefined minimum dose value.

Even though in FIGS. 2-11 there is only illustrated a single blocking member 66 it is generally conceivable to provide two or even more blocking members 66 around the circumference of the display member 60. If two or more blocking members are provided, an equivalent number of blocking threads will be needed.

Figure 9:
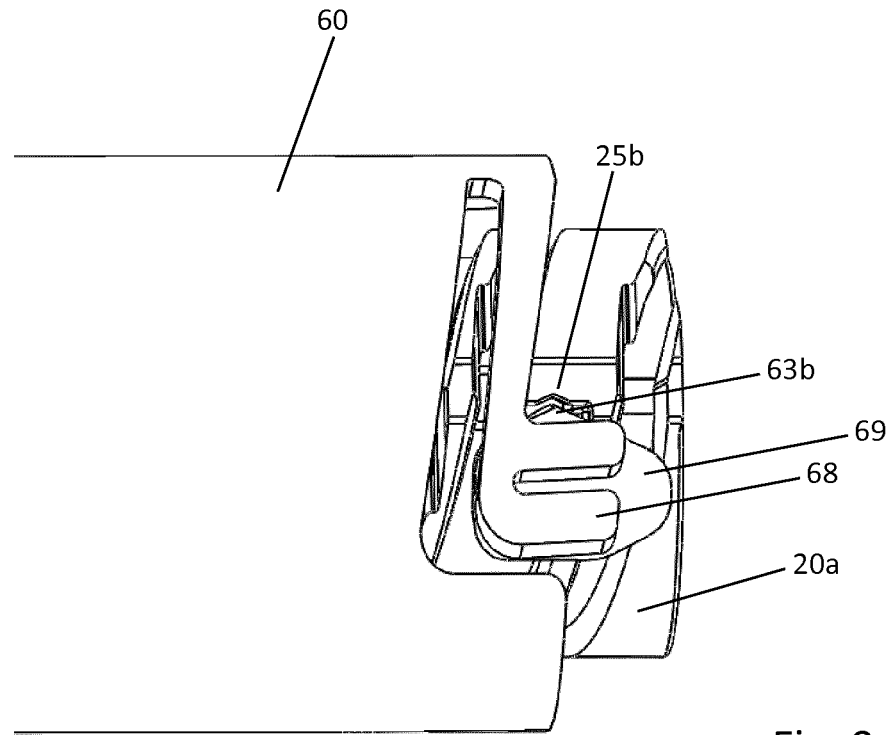
FIG. 9 is illustrative of the maximum dose configuration of the display member.
Figure 10:
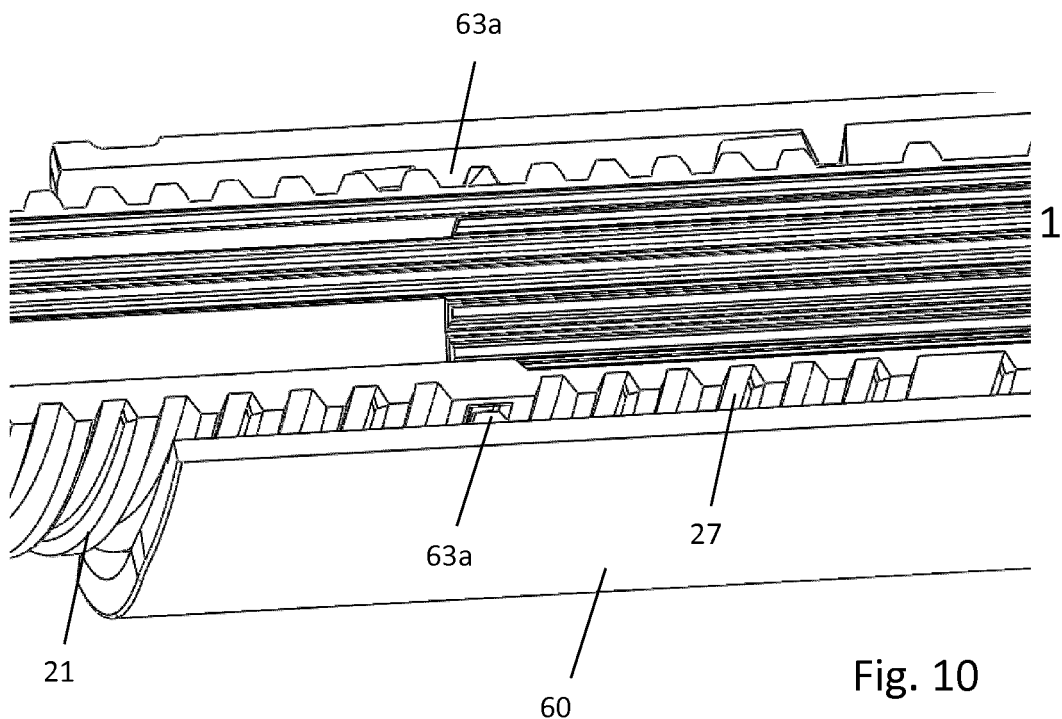
FIG. 10 shows a cross section through display member and inner body.

In FIG. 9 a maximum dose configuration is illustrated, wherein a maximum dose stop 63*b* located on a tangentially facing sidewall of the blocking member 66 tangentially abuts with a correspondingly-shaped stop 25*b* of the inner body.

The arrangement of inner body 20 and display member 60 comprises two pairs of mutually corresponding stops. As shown in FIG. 3, the inner body 20 comprises a distally located maximum stop 25*a* and a proximally located maximum stop 25*b*. Both stops extend radially outward from the circumference of the inner body's 20 elongated shaft 28 and comprise an abutment surface facing in tangential direction. The respective abutment surface coincides with the radial and axial plane. The display member 60 also comprises at least one proximal maximum dose stop 63*b* and at least one distal maximum dose stop 63*a* as shown in FIG. 11. In the embodiment shown in FIG. 11 two distal maximum dose stops 63*a* are provided that mate and engage with correspondingly-shaped dose stops 25*a* on the inner body 20. The mutually corresponding stops 25*a*, 25*b*, 63*a*, 63*b* simultaneously engage as the display member 60 has reached a maximum dose configuration. The mutually engaging stops 25*a*, 25*b*, 63*a*, 63*b* then prevent any further dose incrementing rotation of the display member 60 relative to the inner body 20.

It is generally sufficient to provide only one pair of maximum dose stops, e.g. 25*a*, 63*a*. The two pairs of mutually corresponding maximum dose stops 25*a*, 25*b*, 63*a*, 63*b* reinforce each other. Consequently, the load to be expected on the respective blocking member when reaching the block configuration is lower than it would be when only one pair of mutually corresponding stops, e.g. pair 25*a*, 63*a* would be implemented. This has the advantage, that the stop features can be designed rather smaller than might otherwise be the case. This does not only save space, but also facilitates the device assembly, namely when the display member 60 is threaded onto the inner body 20. Comparatively small stops 25*a*, 25*b*, 63*a*, 63*b* are less prone to fracture or damage during assembly.

Since the minimum as well as the maximum deliverable dose volume only depends on the geometry and the overall design of the inner body 20, its blocking thread 27 and the location of maximum dose stops 25*a*, 25*b* different device types can be easily configured for various applications. Also different dose sizes can be easily implemented by changing only one component. Since the minimum and maximum dose features do not protrude beyond a basic envelope of the inner body it is even straight forward to implement the minimum and maximum dose function with a wide range of different device configurations using common automated assembly equipment.

Figure 3B:
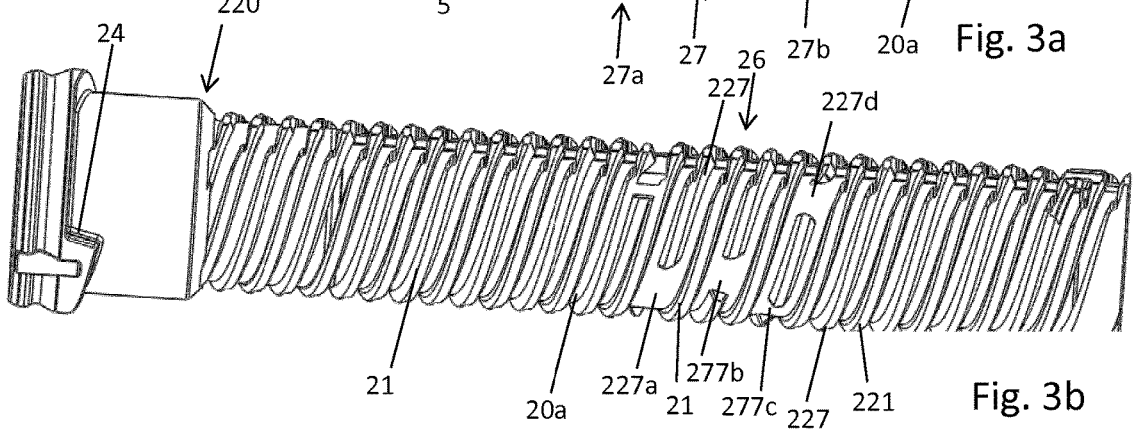
FIG. 3b is an isolated perspective view of an alternative embodiment of the inner body.

In FIG. 3*b* an alternative embodiment of an inner body 220 is shown having a blocking structure 26 with a blocking thread 227 that slightly differs from the blocking thread 27 as shown in FIG. 3*a*. The blocking thread 227 has several recesses 227*a*, 227*b*, 227*c*, 227*d* or interrupts that define discrete dose sizes to be exclusively dispensed by means of the respective drive mechanism. The blocking thread 227 extends almost all along the axial extension of the shaft 20*a*. Only when the position of the blocking member 66 axially and/or tangentially overlaps with a position of one of the recesses 227*a*, 227*b*, 227*c*, 227*d*, the dose member 70 and hence the blocking member 66 is displaceable in distal direction 4 to initiate a dispensing action.

The tangential and axial positions of the recesses 227*a*, 227*b*, 227*c*, 227*d* define discrete dose sizes for which the dispensing of a dose is exclusively possible. Simply by modifying or replacing the inner body 20 with a blocking thread 27 by another inner body 220 with a different blocking thread 227 the injection device can be transformed from a device that allows individual setting of doses of variable size to a fixed dose device, or vice versa.

While the embodiment as shown in FIGS. 12 to 26 relates to a disposable injection device the alternative embodiment according to FIGS. 27 to 38 relates to a reusable injection device. The minimum dose function as described with reference to FIGS. 1 to 11 is not further illustrated in FIGS. 12 to 38 just for reasons of simplicity.

Components of the reusable embodiment according to FIGS. 27 to 38 that are identical or similar compared to the embodiment of FIGS. 12 to 26 are denoted with identical or like reference numerals unless stated otherwise. Where components have changes in comparison to the disposable embodiment similar components have been assigned with reference numerals increased by 100. The general concept and structure of the drive mechanism as shown in FIGS. 27 to 38 is similar to the mechanism disclosed in WO 2014/033195 A1, which is incorporated herein by reference. Implementation and adaptation of the minimum dose function as described above in connection with FIGS. 1 to 11 equally applies to the embodiment of FIGS. 27 to 38.

In this embodiment, the driver 140 is a generally tubular element having in the embodiment shown in the Figures three components 141, 142, 143 which are depicted in FIGS. 27, 30, 31, and 33 in more detail. The driver 140 comprises a distal drive sleeve 141, a proximal drive sleeve 142 and a coupler 143. The distal drive sleeve 141 engages with the piston rod thread 32 to drive the piston rod 30 through the inner body 20 during dose delivery. The distal drive sleeve 141 is also permanently connected to the coupler 143 which in turn is releasably engaged through reset clutch features to the proximal drive sleeve 142. The two halves of the drive sleeve 141, 142 are rotationally and axially connected during dialing and dispense, but are decoupled rotationally during device reset so that they can rotate relative to each other.

Figure 33:
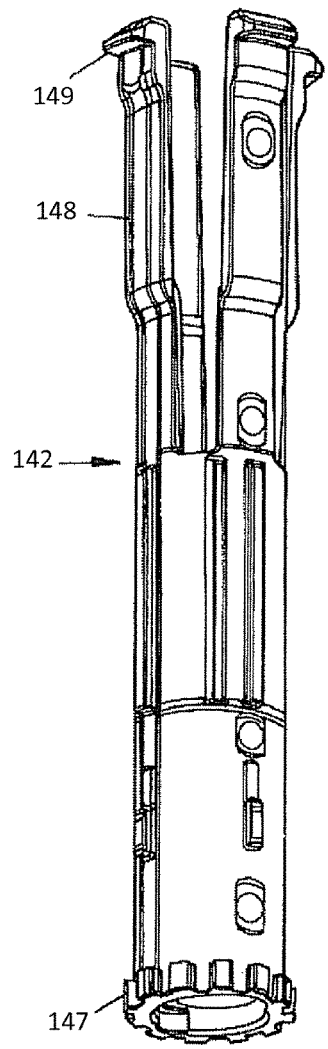
FIG. 33 shows a proximal driver part.
Figure 34:
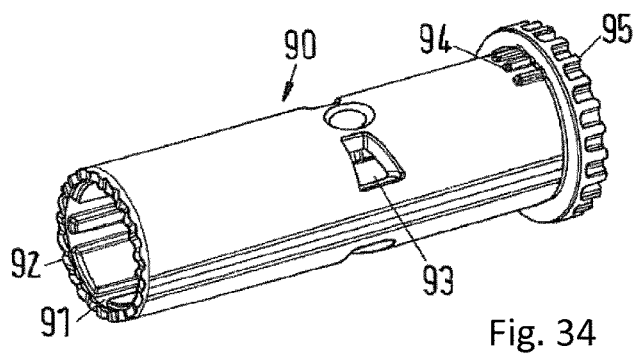
FIG. 34 shows a clutch of the dose member.
Figure 35:
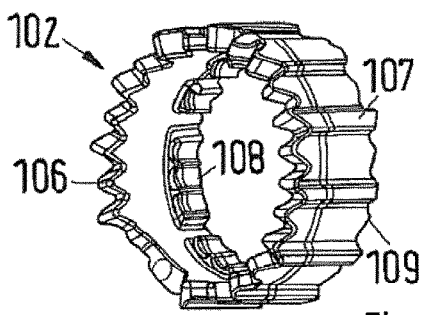
FIG. 35 is an isolated view of a proximal clicker part.
Figure 36:
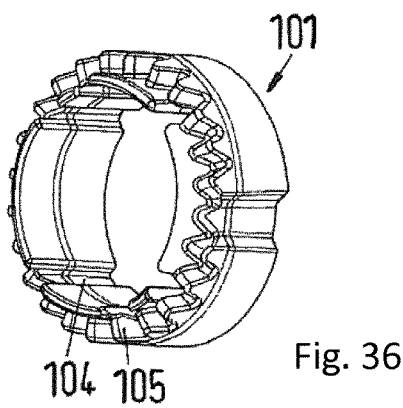
FIG. 36 is an isolated view of a distal clicker part.
Figure 37:
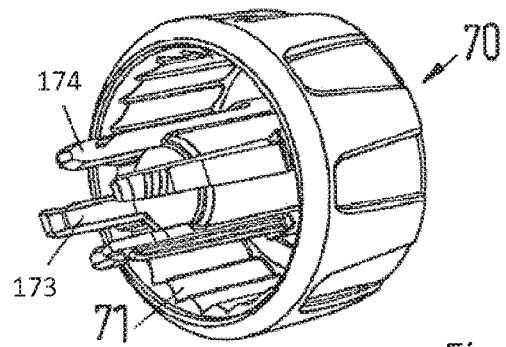
FIG. 37 shows a proximal part of the dose member.
Figure 38:
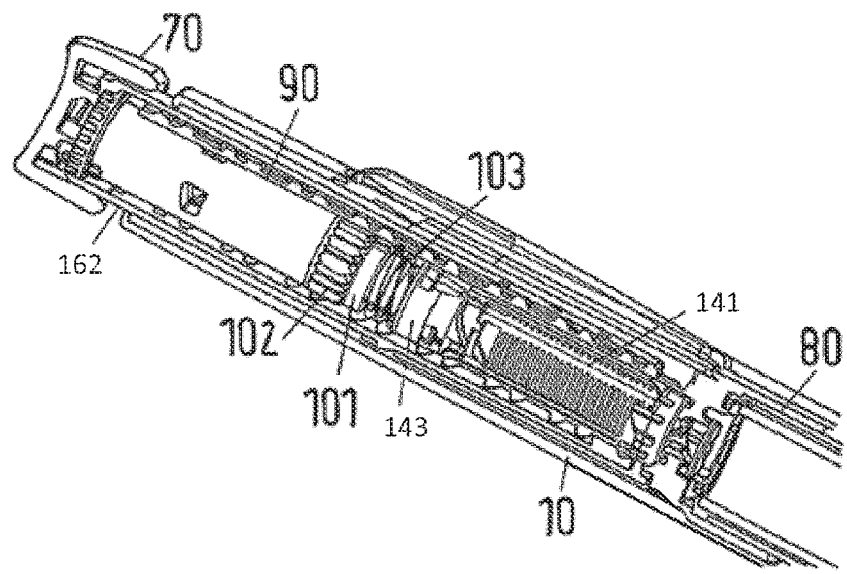
FIG. 38 is a partially cut view through the drive mechanism when assembled in the injection device.

The proximal drive sleeve 142 shown in FIG. 33 supports components of a clicker 100 and sleeve shaped clutch 90 and transfers rotational movement from the dose member 70 to the coupler 142 and distal drive sleeve 141. Teeth features 147 located at the distal end of proximal drive sleeve 142 engage with the reset clutch features on the coupler 143 to connect both halves of the drive sleeve during dialing and dispense. During reset these teeth 147 disengage.

Several splines are provided on the outer surface of proximal drive sleeve 142 engaging with a distal clicker part 101, preventing relative rotation during dialing and dispense. Further splines, which are located in the middle region of proximal drive sleeve 142, engage with the clutch 90 component. They may be arranged to be non-rotationally symmetric so that the various clicker components cannot be assembled accidentally upside down.

The proximal portion of proximal drive sleeve 142 has four arms or fingers 148. A hook-like bearing surface 149 exists on the underside of flange segments on the end of the flexible fingers 148 as seen in FIG. 33. The flexible fingers 148 are separated with gaps or slots that make space for the dose member 70 to snap to the clutch 90 and also enable these fingers to flex inwards during assembly of the proximal drive sleeve 142 to a dial sleeve 162. After assembly the hooks 149 retain the proximal drive sleeve 142 relative to the dial sleeve 162 under the reaction force from the spring 103.

During dispense the dose member 70 depresses the spring 103 via the clutch 90 and the clicker components and this spring 103 is reacted through the coupler 143 to the proximal drive sleeve 142 which then through bearing surfaces 149 applies axial load to the dial sleeve 162. This axial load drives the dial sleeve 162 and hence a number sleeve 161 along the helical thread of the inner body 20, back into the body of the device, until the zero dose stop faces 62 on the number sleeve 161 contact the inner body 20.

Figure 31:
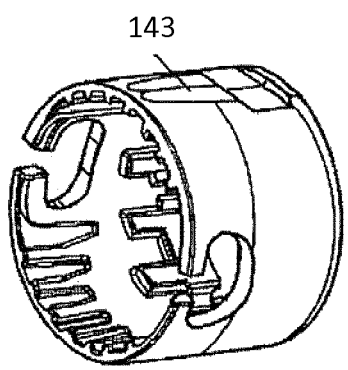
FIG. 31 shows an isolated view of a coupler.
Figure 32:
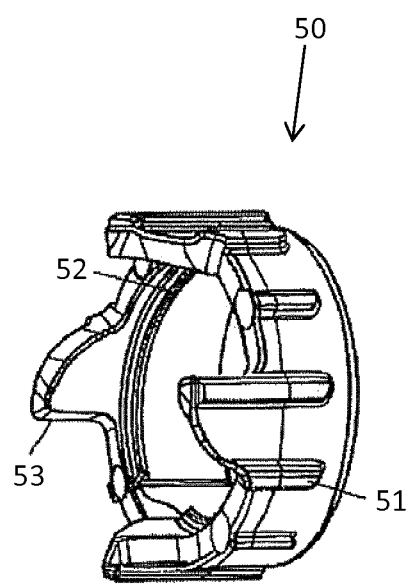
FIG. 32 shows an isolated view a last dose nut.

The coupler 143 shown in FIG. 31 rotationally couples the two halves of the drive sleeve 140 together during dialing and dispense, whilst allowing them to de-couple during reset. The coupler 143 has to also transfer the last dose stop load from the proximal drive sleeve 142 to the distal drive sleeve 141. Two sets of teeth are provided in the coupler 143 for engaging teeth 146 and teeth 147, respectively. The coupler 143 is snapped onto distal drive sleeve 141 allowing limited relative axial movement with respect to the proximal drive sleeve 142.

The display member 160 is a generally tubular element which is composed of a number sleeve 161 and dial sleeve 162 which are snapped together during assembly to axially and rotationally constrain these two components, which thus act as a single part. The dial sleeve 162 is assembled to the number sleeve 161 such that once assembled, no relative movement is allowed. The parts are made as separate components to enable both molding and assembly. Also, whereas the number sleeve 161 is preferably white to give contrast for the e.g. black dose numbers, the dial sleeve 162 color can be chosen to suit the aesthetics or perhaps to distinguish the drug type.

At the proximal end, the dial sleeve 162 has internal clutch features 165 that engage with the clutch component 90 during dialing and disengage from the clutch during dispense. These clutch features 165 rotationally lock the dial sleeve 162 to the clutch 90 during dialing and when the zero and maximum dose stops are engaged. When the dose member 70 is depressed these clutch features disengage to allow the clutch 90 to move axially whilst the dial sleeve 162 and number sleeve 161 spin back to the zero unit start position.

Figure 29:
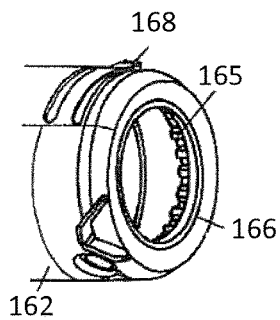
FIG. 29 shows a proximal end of the display member according to FIG. 27.
Figure 30:
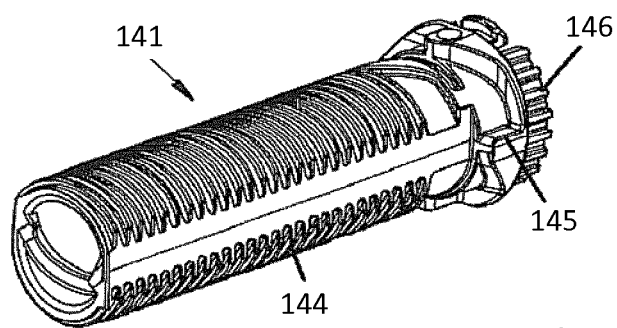
FIG. 30 is an isolated view of a distal driver part according to FIG. 27.

The dial sleeve 162 rotates out during dialing through its engagement with the clutch 90 and number sleeve 161, and rotates back in during dispense under the axial force applied by the proximal drive sleeve 142 to a flange-like bearing face 166 on the proximal end of the dial sleeve as shown in FIG. 29. This bearing face 166 engages with the flexible arms 148 of the proximal drive sleeve 142 during dispense. Two diametrically opposite faces 167 may engage with the outer body 10 when the maximum dose has been dialed, forming the maximum dose stop faces.

A central sleeve-like portion of the dose member 70 is provided with four arms 173 having hook-like snap features 174 at their respective distal ends. The arms 173 form splined surfaces engaging with the clutch 90 to transfer torque from the dose member 70 through the clutch to the dial sleeve 162 and proximal drive sleeve 142. The snap features 174 engage apertures in the clutch 90 and are designed with angled undercut faces to maintain engagement when an axial load is applied to pull the dose member 70 out of the pen body 10. The space between arms 173 defines pockets giving clearance for the flexible arms 148 of proximal drive sleeve 142 to slide freely relative to the dose member 70 and clutch 90 when the dose member 70 is depressed and released during dose dispense.

The tubular clutch 90 is provided between the display member 160 and the dose member 70. The clutch is fixed relative to and retains the dose member 70 and together they travel axially relative to the proximal drive sleeve 142 when the dose member 70 is depressed during dispense, disengaging the clutch teeth 95 from the dial sleeve clutch teeth 165. It also transfers torque from the dose member 70 to the proximal drive sleeve 142, and the dialing and zero and maximum dose stop loads from the dose member 70 via the clutch teeth to the dial sleeve 162 and number sleeve 161.

Drive sleeve splines 91 provided on an inner surface of the clutch engage with the proximal drive sleeve 142. At the distal end face, clutch biasing teeth 92 are provided which mate with similar teeth 109 on the proximal clicker part 102 to ensure that in the unrestrained button out position (dialed dose) the clutch is biased in rotation to the proximal clicker part 102 under the biasing action of the clutch spring 103 thus ensuring that the dose number shown on the display member is correctly and unambiguously displayed to the user. The teeth 92 are shallow in height to prevent the proximal clicker part 102 from engaging with splines on the proximal drive sleeve 142 during dialing. Four snap apertures 93 serve to retain the snap features 174 of the dose member 70. Near its proximal end, the clutch has splines 94 which at the end of dispense with the dose member 70 depressed lock to the inner body 20 to prevent the user from rotating the dose member 70 below the zero dose position.

Clutch teeth 95 engage with clutch teeth 165 of the dial sleeve 162 to rotationally couple the dose member 70 via the clutch to the number sleeve 161. During dispense the clutch 90 is moved axially so as to disengage these clutch teeth 95 releasing the dial sleeve 162 to rotate back into the device whilst the clutch 90 and hence driver 140 move axially to dispense the dose.

The clicker 100 comprises a distal clicker part 101, a proximal clicker part 102 and a spring 103. The spring 103 serves to bias the dose member 70 out so that at the end of a dose the dose member 70, in particular its proximal button portion pops out, re-engaging the clutch 90 with the dial sleeve 162 ready for dialing. Further, it provides the spring force for the clicker components to provide audible and tactile feedback to the user and also provides detent positions for the number sleeve 161. In addition, it holds the two halves of the drive sleeves 141, 142 in rotational engagement during dialing and dispense, whilst allowing them to disengage during device reset.

The distal clicker part 101 is permanently splined to the proximal drive sleeve 142 and engages with the proximal clicker part 102 which in turn is splined to the inner body 20. During dialing when the drive sleeve is rotated relative to the inner body 20, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the axial dispense load applied by the user to the dose member 70 and this prevents relative rotation between the proximal drive sleeve 142 and inner body 20, driving the piston rod 30 forwards to deliver the dose. The splines 104 on the inner bore rotationally couple the distal clicker part 101 to the proximal drive sleeve 142 at all times, but allow free axial movement when the dose member 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body 20 during both dialing and dispense, providing clicks during dialing and locking the proximal drive sleeve 142 in rotation during dispense. Additional cylindrically shaped splines 108 also couple the proximal clicker part 102 rotationally to the proximal drive sleeve 142 when the dose member 70 is depressed, this preventing the user from dialing past 80 units with the dose member 70 depressed. Proximal clicker part 102, in addition to the primary clicker teeth 106, has clutch biasing teeth 109 on the opposite end face. These teeth mate with similar teeth 92 on the clutch 90 to ensure that in the unrestrained button out position (dialed dose) the clutch is biased in rotation by the proximal clicker part 102 under the biasing action of clutch spring 103.

The cartridge bias spring 110 is assembled as two components one after the other, the lower first and the upper second. The spring combination serves to apply an end load to the cartridge 80 at extremes of tolerance so as to bias it forwards onto the end face of the ferrule in the cartridge holder 11. This ensures that when the user removes and attaches a needle, the friction between the needle cannula and septum of the cartridge 80 does not move the cartridge 80 axially relative to the cartridge holder 11. The bias spring 110 also acts to provide a force against which the user has to connect the cartridge holder 11 and this may add to the tactile feedback of a bayonet joint between cartridge holder 11 and inner body 20. The spring 100 also serves to eject the cartridge holder 11 if the cartridge holder is not correctly attached in a secure position, highlighting this error to the user.

During dose setting the dose member 70, driver 140 and display member 160 are rotationally locked together via clutch 90. Further, dose member 70, driver 140 and display member 160 are axially coupled. Thus, these three components wind out of the outer body 12 during dose setting. Clockwise rotation of the button dose member 70 causes the driver 140 to rotate on a helical path and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

With the desired dose dialed, the device 1 is ready for dose dispensing. This requires pushing the proximal button portion of the dose member 70 which will result in a disengagement of the clutch 90 from dial sleeve 162 thus allowing relative rotation between the display member 160 and the dose member 70. In all conditions the driver 140 and the dose member 70 are rotationally locked together by engagement of arms 173 and fingers 148 and by splines 91 engaging corresponding splines on proximal drive sleeve 142. Thus, with the clutch 90 disengaged dose member 70 and driver 140 is rotationally locked together with the dose member 70, the driver 140 and the display member 160 still being axially coupled.

When dispensing a dose, the dose member 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the drive sleeve 140 and clutch 90 parts of the mechanism are forced to move axially whilst the dial sleeve 162 and number sleeve 161 are free to spin back into the outer housing 10. The interaction of mating threads between the piston rod 30, driver 140 and inner body 20 delivers a mechanical advantage of, for example 2:1.

In other words, axially advancing driver 40 causes the piston rod 30 to rotate which due to the threaded engagement of piston rod 30 with the inner body 20 advances the piston rod 30. During dose dispensing dispense clicker 168, 71 is active which involves dose member 70 and display member 160. The dispense clicker provides primarily audible feedback to the user that the medicament is being dispensed.

When dispensing of a dose is complete and when the user removes the force from the end of the dose member 70, the clutch spring 103 pushes this dose member 70 proximally, re-engaging the teeth 165 and 95 between the clutch and the dial sleeve.

Resetting the device starts with removal of the cartridge holder 11 and replacing an empty cartridge with a full cartridge 80. As the cartridge holder 11 is re-attached, the bung of the new cartridge 80 contacts bearing 33, thus pushing piston rod 30 back into the housing. Initially, the piston rod 30 screws into the inner body 20, thereby axially disengaging the coupler 143 from the proximal drive sleeve 142 against the biasing force of spring 103. Once disengaged the coupler 143 is free to start rotating together with distal drive sleeve 141 and continues to do so as the cartridge holder 11 is moved axially into engagement with the inner body 20. Thus, the distal drive sleeve 141 rotates with respect to the proximal drive sleeve 142 which is still rotationally constrained in inner body 20 as clicker parts 101 and 102 are pressed together by compressed spring 103.

As the distal drive sleeve 141 rotates, last dose nut 50 is reset to its (distal) start position. The last dose nut 50 is threadedly engaged with an outer thread 144 of the distal drive sleeve 141. Coupling the cartridge holder 11 to inner body 20 backs off the mechanism due to the bayonet structure allowing re-engagement of the proximal drive sleeve 142 with coupler 143 and thus the distal drive sleeve 141.

It is to be noted here, that the minimum dose function as described in connection with FIGS. 1 to 11 is equally implementable or is actually implemented with the reusable device as described in connection with FIGS. 27 to 38.

The display member 160 as it is implemented with the injection device 1 and with the drive mechanism according to FIGS. 27-38 is illustrated separately. The display member 160 comprises a number sleeve 161 and a dial sleeve 162. The dial sleeve 162 is provided with the ratchet arm 168 near a proximal end and further has the bearing face 166 and the clutch feature 165 to selectively engage with the teeth 95 of the clutch 90. The number sleeve 161 and the dose sleeve 162 are permanently and mutually engaged. A distal section of the dial sleeve 162 is located inside a proximal section of the number sleeve 161. Hence, the sidewall of the number sleeve 161 encloses at least a distal portion of the sidewall of the dial sleeve 162.

There are provided mutually corresponding recesses and protrusions on the radially overlapping portions of the number sleeve 161 and the dial sleeve 162. In the illustrated embodiment there are provided at least two recesses near a proximal end of the number sleeve 161 that engage with and receive radially outwardly extending protrusions on a distal section of sidewall of the dial sleeve 162. In this way a snap-fit engagement between number sleeve 161 and dial sleeve 162 is obtained. The dial sleeve 162 is therefore permanently rotationally and axially locked to the number sleeve 161 and vice versa.

In one embodiment there are provided two blocking members 66 at a proximal end of the number sleeve 161. The radially inwardly extending protrusions 67 of the blocking members 66 each extend through an aperture of the sidewall of the dial sleeve 162. In this way the protrusions 67 and hence the blocking members 66 extends radially through the sidewall of the dial sleeve 162 in order to directly engage with the blocking structure 26 on the outer circumference of the inner body 20. The longitudinal or axial extension of the aperture is large enough so as to allow and to support an axial displacement of the blocking member 66 with regard to the dial sleeve 162 and with regard to the number sleeve 161 when in a release configuration R.

In the release configuration R the protrusion 67 of the blocking member 66 is located distally from the blocking structure 26 and hence distally from the blocking thread 27. In other words the blocking member 66 may be in alignment with an intersection or gap of the blocking thread 27. In the release position or release configuration R the dose member 70 is displaceable in distal direction 4 thereby urging the flexible blocking member 66 in distal direction.

In a blocking position B the protrusion 67 of the blocking member 66 is located on a proximal side of the blocking structure 26. Here, a distal edge 67d of the protrusion 67 faces a proximal edge 27e of the blocking thread 27. In this blocking position B the blocking member 66 is in axial abutment with the blocking structure 26. The blocking member 66 cannot be displaced in distal direction 4. A distally directed dispensing force acting on the dose member 70 transfers via the abutment 76 and 68 into the blocking member 66. Said force is reacted through the mutual axial abutment of the correspondingly-shaped proximal and distal edges 27e, 67d thereby preventing and impeding a distally directed displacement of the blocking member 66.

With the further embodiment of the display member 260 there is implemented the same interaction and positive engagement between the number sleeve and the dial sleeve and between the dose member 70, the blocking members 66 and the inner body 20. There is only one exception in that the blocking members 66 are located on the dial sleeve rather than on the number sleeve 161. Here, the dial sleeve and/or the number sleeve comprises an aperture of a recess like the aperture of the dial sleeve 162 to support and to provide a direct mechanical interaction between the blocking member 66 and the blocking structure 26.

With this embodiment the number sleeve and the elastic blocking members 66 can be made from different materials. Since the number sleeve is typically provided with numbers or symbols on its outer circumference to indicate a size of a dose in the window 14 of the outer body 12 a material can be selected and used for the number sleeve that is particularly suitable for printing or coating. For the blocking members 66 and for the dial sleeve integrally formed with the blocking members 66 a different plastic material can be chosen that provides desirable or optimized mechanical properties for the elastic deflection of the blocking members 66. For instance, the dial sleeve and the blocking members 66 can be made from POM.

LIST OF REFERENCE NUMBERS 1 injection device
2 hub
3 cover 4 distal direction
5 proximal direction
10 housing
11 cartridge holder
12 outer body
13 layer
14 window
15 aperture
16 thread
20 inner body
20a shaft
21 outer thread
22 spline
23 inner thread
24 stop
25a, b stop
26 blocking structure
26a distal end
26b proximal end
27 blocking thread
27a distal end
27b proximal end
27c chamfer
27d distal edge
27e proximal edge
30 piston rod
31 outer thread
32 outer thread
33 bearing
40 driver
41 thread
42 inner thread
43 opening
44 finger
45 protrusion
46 flap
47 stop
50 last dose nut
51 external rib
52 inner thread
53 stop
60 display member
60a sidewall
60b proximal part
61 inner thread
62 stop
63a stop
63b stop
64 teeth
65 flexible arm
66 blocking member
66a slit
66b free end
66c base portion
67 protrusion
67d distal edge
68 abutment
69 support face
70 dose member
70a sleeve portion
71 dose dial/dose button
72 sleeve-like part
73 rib
73a recess
74 teeth
75 toothed profile
76 abutment
80 cartridge
81 reservoir
82 bung
83 crimped metal cap
90 clutch
91 splines
92 teeth
93 aperture
94 splines
95 teeth
100 clicker
101 distal clicker
102 proximal clicker
103 clutch spring
104 splines
105 clicker teeth
106 clicker teeth
107 splines
108 splines
109 teeth
110 cartridge bias spring
120 cap
140 driver
141 distal drive sleeve
142 proximal drive sleeve
143 coupler
144 thread
145 stop
146 teeth
147 teeth
148 flexible finger
149 hook
160 display member
161 number sleeve
162 dial sleeve
165 clutch feature
166 bearing face
167 stop
168 ratchet arm
173 arm
174 snap feature
220 inner body
227 blocking thread
227a recess
227b recess
227c recess
227d recess

The invention claimed is:

1. A drive mechanism for an injection device for setting and dispensing of a dose of a medicament, the drive mechanism comprising: an inner body fixable inside a housing of the injection device, the inner body comprising an elongated shaft extending in an axial direction and having an outer thread;
a tubular-shaped display member having an inner thread engaged with the outer thread of the inner body; and
a dose member axially displaceable between a dose setting position and a dose dispensing position relative to the display member,
wherein the display member comprises at least one blocking member movable in axial direction between a blocking position and a release position and engageable with a blocking structure on the outer circumference of the inner body,
wherein when in blocking position the blocking member axially engages with the dose member and with the blocking structure to block an axial displacement of the dose member from the dose setting position towards the dose dispensing position.

2. The drive mechanism according to claim 1, wherein the blocking structure comprises a blocking thread axially extending on the elongated shaft of the inner body, wherein the blocking thread (27; 227) and the outer thread (21; 221) have the same pitch.

3. The drive mechanism according to claim 2, wherein a distal end of the blocking thread is chamfered.

4. The drive mechanism according to claim 3, wherein, when rotating the display member in a dose incrementing direction, the protrusion of the blocking member slides along the chamfer of the blocking thread's distal end:
   i) to flex the blocking member's free end section from its release position in proximal direction towards its blocking position, or
   ii) to axially abut with the blocking thread's proximally facing edge.

5. The drive mechanism according to claim 3, wherein, when rotating the display member in a dose dispensing direction with the blocking member in release position, the protrusion of the blocking member slides along a distal edge of the blocking thread as the blocking member passes the blocking thread's proximal end when entering the blocking thread.

6. The drive mechanism according to claim 3, wherein the blocking thread comprises at least one recess having a size to receive the blocking member or its radially inwardly extending protrusion.

7. The drive mechanism according to claim 1, wherein the blocking member comprises a flexible arm extending in a tangential direction along the circumference of the display member.

8. The drive mechanism according to claim 1, wherein the blocking member comprises a radially inwardly extending protrusion at a free end section to engage with the blocking structure.

9. The drive mechanism according to claim 1, wherein the blocking member comprises an abutment at its free end section facing in axial direction to axially abut with a corresponding abutment of the dose member.

10. The drive mechanism according to claim 1, wherein the axial position of a distal end of the blocking structure on the inner body defines a maximum size of a dose for a priming procedure.

11. The drive mechanism according to claim 1, wherein the axial position of a proximal end of the blocking structure on the inner body defines a minimum size of a therapeutic dose.

12. The drive mechanism according to claim 1, wherein the display member comprises a number sleeve and a dial sleeve, and wherein the at least one blocking member is located on the dial sleeve or wherein the at least one blocking member is integrally formed with the dial sleeve.

13. The drive mechanism according to claim 1, wherein the inner body comprises at least a first maximum dose stop at its outer circumference to engage with first and second radially inwardly extending maximum dose stops of the display member, respectively, when the display member arrives in a maximum dose position.

14. The drive mechanism according to claim 1, further comprising a piston rod and a tubular-shaped driver extending in axial direction, wherein the piston rod comprises a first outer thread engaged with an inner thread of the inner body and comprises a second outer thread of opposite hand engaged with an inner thread of the driver.

15. The drive mechanism according to claim 14, wherein the dose member is permanently splined with the driver which is selectively rotationally lockable to the inner body by displacing the dose member into the dose dispensing position and wherein the dose member and the display member are selectively rotationally lockable and releasable via a clutch rotationally engaging the dose member and the display member when the dose member is in dose setting position and rotationally releasing the dose member and the display member when the dose member is in dose dispending position.

16. An injection device for setting and dispensing of a dose of a medicament, comprising: a housing (10) comprising a drive mechanism for an injection device for setting and dispensing of a dose of a medicament, the drive mechanism comprising:
   an inner body fixable inside a housing of the injection device, the inner body comprising an elongated shaft extending in an axial direction and having an outer thread;
   a tubular-shaped display member having an inner thread engaged with the outer thread of the inner body; and
   a dose member axially displaceable between a dose setting position and a dose dispensing position relative to the display member,
   wherein the display member comprises at least one blocking member movable in axial direction between a blocking position and a release position and engageable with a blocking structure on the outer circumference of the inner body,
   wherein when in blocking position the blocking member axially engages with the dose member and with the blocking structure to block an axial displacement of the dose member from the dose setting position towards the dose dispensing position; and
   a cartridge arranged inside the housing and filled with a liquid medicament.

17. The injection device of claim 16, wherein the liquid medicament comprises a pharmaceutically active compound.

* * * * *